United States Patent
Miyashita et al.

(10) Patent No.: US 7,972,285 B2
(45) Date of Patent: Jul. 5, 2011

(54) MOTOR FUNCTION MEASURING SENSOR, MOTOR FUNCTION MEASURING APPARATUS, AND MOTOR FUNCTION ANALYZING APPARATUS

(75) Inventors: Tsuyoshi Miyashita, Fuchu (JP); Akihiko Kandori, Tokyo (JP); Mitsuru Onuma, Tokyo (JP); Norihiko Matsumoto, Minamiashigara (JP); Kouichi Ishizuka, Odawara (JP); Norihiko Adachi, Chigasaki (JP); Atsushi Ninomiya, Ome (JP); Yoshimi Kasai, Kokubunji (JP)

(73) Assignee: Hitachi Computer Peripherals Co., Ltd., Kanagawa (JP)

( * ) Notice: Subject to any disclaimer, the term of this patent is extended or adjusted under 35 U.S.C. 154(b) by 583 days.

(21) Appl. No.: 12/028,041

(22) Filed: Feb. 8, 2008

(65) Prior Publication Data
US 2008/0238414 A1 Oct. 2, 2008

(30) Foreign Application Priority Data
Mar. 30, 2007 (JP) ................................ 2007-094512

(51) Int. Cl.
*A61B 5/103* (2006.01)
(52) U.S. Cl. .......................................................... 600/595
(58) Field of Classification Search .................... 600/595
See application file for complete search history.

(56) References Cited

U.S. PATENT DOCUMENTS

| 5,660,567 | A * | 8/1997 | Nierlich et al. | 439/620.21 |
| 6,070,269 | A * | 6/2000 | Tardif et al. | 2/69 |
| 6,166,653 | A * | 12/2000 | Schulmeyer et al. | 340/9.16 |
| 6,287,304 | B1 * | 9/2001 | Eggers et al. | 606/37 |
| 6,837,725 | B1 * | 1/2005 | Gordon et al. | 439/188 |
| 7,647,097 | B2 * | 1/2010 | Flaherty et al. | 600/544 |
| 2002/0096391 | A1 * | 7/2002 | Smith et al. | 181/135 |
| 2004/0046675 | A1 * | 3/2004 | Murata | 340/686.1 |
| 2006/0000849 | A1 * | 1/2006 | Simmons et al. | 222/1 |
| 2007/0021644 | A1 * | 1/2007 | Woolson et al. | 600/9 |
| 2007/0038154 | A1 * | 2/2007 | Kandori et al. | 600/595 |
| 2007/0257165 | A1 * | 11/2007 | Newbould et al. | 248/205.3 |
| 2008/0027509 | A1 * | 1/2008 | Andino et al. | 607/50 |
| 2008/0119753 | A1 * | 5/2008 | Ricciardelli et al. | 600/532 |

FOREIGN PATENT DOCUMENTS
JP 11056442 A * 3/1999
* cited by examiner

*Primary Examiner* — Max Hlndenburg
*Assistant Examiner* — M. Stout
(74) *Attorney, Agent, or Firm* — Antonelli, Terry, Stout & Kraus, LLP.

(57) ABSTRACT

A motion sensor for measuring motion information of a subject comprises a coil substrate having transmitting or receiving coils piled one on top of another and a holder in which the coil substrate is mounted. Formed on the holder are curved surfaces to which an adhesive sheet is stuck and at which the holder is attached to a nail of a subject via the adhesive sheet. Further, there is provided a casing where first and second containing space are formed to contain measurement instruments including an adhesive member where a plurality of the adhesive sheets are laid one on top of another, the motion sensor, and the like.

9 Claims, 42 Drawing Sheets

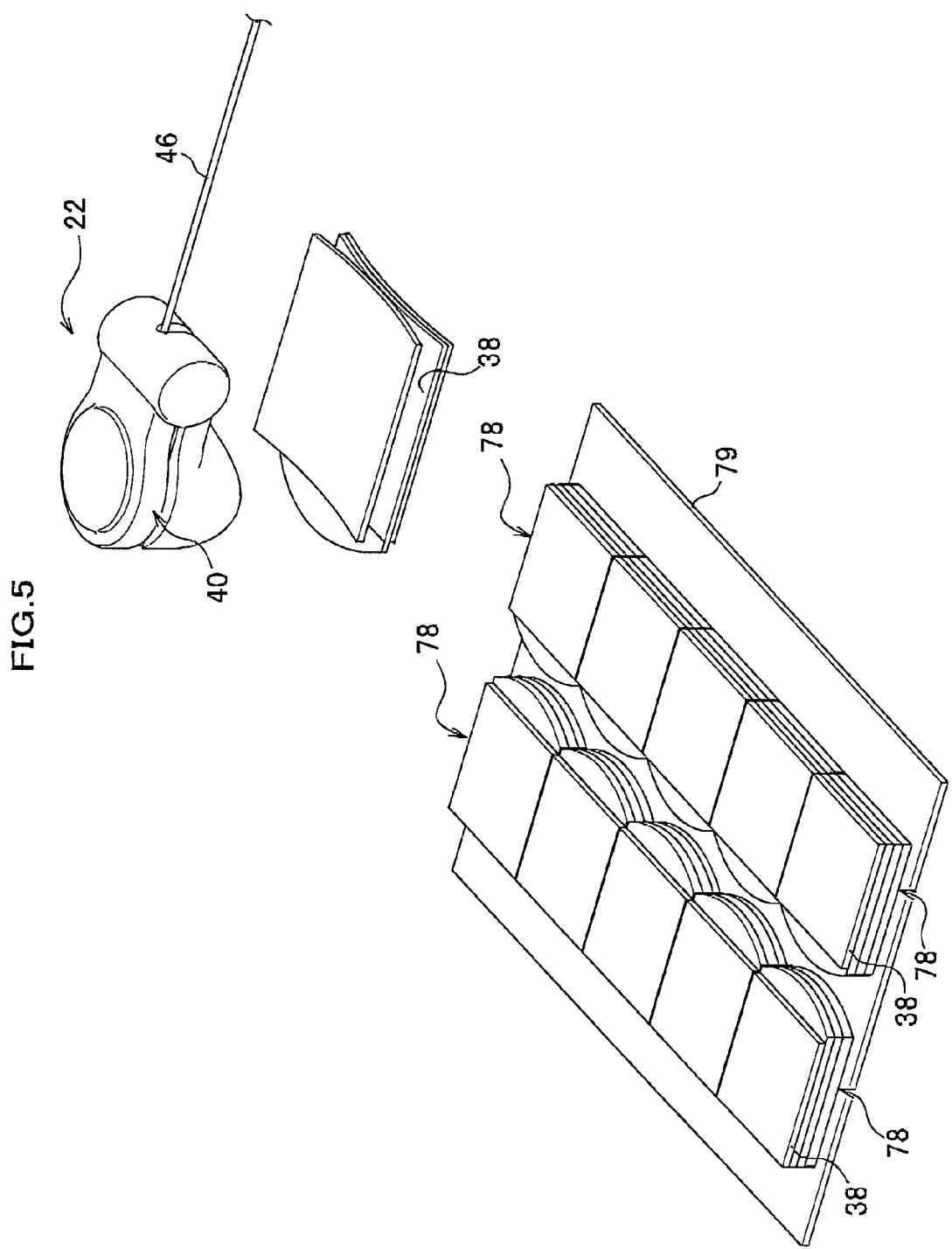

FIG.27

MOTOR FUNCTION MEASUREMENT-MAIN

2702 MEASUREMENT DATA LIST PORTION
2700 CONTROL SCREEN IMAGE
2708

MEASUREMENT DATA  ○ SUBJECT DATA  ● MEASUREMENT DATA

| SUBJECT ID | FULL NAME | MEASUREMENT DATE | MEASUREMENT TIME | MEASUREMENT INTERVAL | MEASUREMENT METHOD | AGE | SEX | COMMENT 1 | COMMENT 2 |
|---|---|---|---|---|---|---|---|---|---|
| ID000001 | Tarou Hitachi | 2006/02/22 | 11:24:22 | 20 sec | Both Hands | 53 | Male | Very tired | Lack of Sleep |
| ID000001 | Tarou Hitachi | 2006/09/21 | 14:31:56 | 10 sec | Left Hand | 53 | Male | | |
| ID000001 | Tarou Hitachi | 2006/10/05 | 14:42:45 | 10 sec | Left Hand | 53 | Male | Headachy | |
| ID000001 | Tarou Hitachi | 2006/10/19 | 14:44:40 | 20 sec | Right Hand | 53 | Male | | |
| ID000001 | Tarou Hitachi | 2006/11/01 | 14:46:31 | 30 sec | Both Hands | 53 | Male | Right hand | |
| ID000001 | Tarou Hitachi | 2006/11/15 | 14:48:13 | 20 sec | Both Hands | 53 | Male | | |
| ID000001 | Tarou Hitachi | 2006/11/29 | 14:49:46 | 60 sec | Both Hands | 53 | Male | | |
| ID000001 | Tarou Hitachi | 2006/12/14 | 15:08:38 | 10 sec | Left Hand | 53 | Male | | |
| ID000001 | Tarou Hitachi | 2006/12/28 | 15:10:30 | 20 sec | Right Hand | 53 | Male | | |
| ID000001 | Tarou Hitachi | 2007/01/11 | 15:13:57 | 30 sec | Both Hands | 53 | Male | | |
| ID000001 | Tarou Hitachi | 2007/01/25 | 15:16:18 | 20 sec | Both Hands | 53 | Male | | |
| ID000001 | Tarou Hitachi | 2007/02/08 | 15:18:28 | 60 sec | Both Hands | 53 | Male | | |
| ID000001 | Tarou Hitachi | 2007/02/22 | 16:33:22 | 60 sec | Left Hand | 53 | Male | | |
| ID000002 | Hanako Hitachi | 2022/02/07 | 16:33:22 | 60 sec | Left Hand | 53 | Female | | |

SEARCH CONDITION
SUBJECT ID
FULL NAME                    MEASUREMENT DATE  [   ] ~ [   ]
SEX      [ ▽ ]               MEASUREMENT METHOD [    ▽ ]
AGE      [   ] ~ [   ]       COMMENT 1
                             COMMENT 2

[SEARCH START]
[CLEAR CONDITIONS]

2704 SEARCH CONDITION INPUTTING PORTION

MAIN SCREEN IMAGE (MEASUREMENT DATA LIST SCREEN IMAGE)

OPERATIONS
[NEW MEASUREMENT] — 2720 (FIRST CONTROL)
[MEASUREMENT] — 2722 (FIRST CONTROL)
[DATA ANALYSIS] — 2724 (SECOND CONTROL)
[INTER-ANNUAL DISPLAY] — 2726 (THIRD CONTROL)
[MEASUREMENT DATA DELETION]
[EXPORT]
TOOLS
[DATA MANAGEMENT]
[OPTION]
[END]

2706 OPERATION (FUNCTION) BUTTON PORTION

FIG.28

MOTOR FUNCTION MEASUREMENT-MAIN 2720 (FIRST CONTROL)
2722 (FIRST CONTROL)
2806 OPERATION (FUNCTION) BUTTON PORTION

OPERATIONS
- NEW MEASUREMENT
- MEASUREMENT

SUBJECT INFORMATION SETTINGS
- ADDITION
- CHANGE
- DELETION

TOOLS
- DATA MANAGEMENT
- OPTION
- END

⦿ SUBJECT DATA    ○ MEASUREMENT DATA

2708

SUBJECT DATA

| SUBJECT ID | FULL NAME | BIRTH DATE | SEX | DOMINANT HAND | MEMO |
|---|---|---|---|---|---|
| ID000001 | Tarou Hitachi | 1953/12/25 | Male | Left Hand | Sample data |
| ID000002 | Hanako Hitachi | 1955/11/25 | Female | Right Hand | |
| ID000003 | Jirou Hitachi | 1954/08/25 | Male | Both Hands | |
| ID000004 | Tugiko Hitachi | 1955/09/05 | Female | Right Hand | |
| ID000005 | Saburou Hitachi | 1956/09/15 | Male | Left Hand | |
| ID000006 | Miko Hitachi | 1957/08/26 | Female | Unknown | |
| ID000007 | Sirou Hitachi | 1958/10/07 | Male | Both Hands | |
| ID000008 | Yotuko Hitachi | 1959/10/18 | Female | Right Hand | |
| ID000009 | Gorou Hitachi | 1960/10/28 | Male | Left Hand | |
| ID000010 | Ituko Hitachi | 1961/11/08 | Female | Unknown | |
| ID000011 | Muturou Hitachi | 1962/11/19 | Male | Both Hands | |
| ID000012 | Mutuko Hitachi | 1963/11/30 | Female | Right Hand | |
| ID000013 | Sitirou Hitachi | 1964/12/10 | Male | Left Hand | |
| ID000014 | Nanako Hitachi | 1965/12/21 | Female | Unknown | |
| ID000015 | Hatirou Hitachi | 1967/01/01 | Male | Both Hands | |
| ID000016 | Yatuko Hitachi | 1968/01/12 | Female | Right Hand | |
| ID000017 | Kyuurou Hitachi | 1969/01/22 | Male | Left Hand | |
| ID000018 | Kyuuko Hitachi | 1970/02/02 | Female | Both Hands | |
| ID000019 | Jyuurou Hitachi | 1971/02/13 | Male | Both Hands | |

2802 SUBJECT DATA LIST PORTION

SEARCH CONDITION
- SUBJECT ID
- FULL NAME
- SEX

SEARCH START
CLEAR CONDITIONS

2804 SEARCH CONDITION INPUTTING PORTION

MAIN SCREEN IMAGE (SUBJECT DATA LIST SCREEN IMAGE)

FIG.29

| MOTOR FUNCTION MEASUREMENT-SUBJECT INFORMATION SETTINGS | ☒ |
|---|---|

PLEASE SET SUBJECT INFORMATION

SUBJECT ID [　　　　　]
FULL NAME [　　　　　]
BIRTH DATE [2007/03/08 ▼]
SEX　　　　⦿ Male　○ Female
DOMINANT HAND ⦿ Left Hand　○ Right Hand　○ Both Hands　○ Unknown
MEMO [　　　　　　　　　　　]

[ACQUISITION OF INFORMATION FROM SUBJECT ID]　[SAVE]　[CLOSE]

SUBJECT INFORMATION SETTINGS SCREEN IMAGE

FIG.30

MOTOR FUNCTION MEASUREMENT-MEASUREMENT SETTINGS

SUBJECT INFORMATION
- SUBJECT ID: ID000001
- FULL NAME: Tarou Hitachi
- BIRTH DATE: 1953/12/25
- SEX: Male
- DOMINANT HAND: Left Hand
- MEMO: Sample data MEASUREMENT METHOD
⦿ Left Hand  ○ Right Hand  ○ Both hands (simultaneously)  ○ Both hands (anti-phase)

MEASUREMENT TIME
⦿ 10 sec  ○ 20 sec  ○ 30 sec  ○ 60 sec  ○ Free [ ]

CALIBRATION INFORMATION

| Left hand | Right hand |
|---|---|
| 20mm | 20mm |
| 30mm | 30mm |
| 60mm | 60mm |
| MAXIMUM | MAXIMUM |

- SETTING OF SUBJECT INFORMATION — 3012
- SETTING FOR CALIBRATION — 3014
- PERFORMING OF MEASUREMENT — 3016
- ANALYSIS RESULT — 3018

MEASUREMENT COMMENTS
- COMMENT 1
- COMMENT 2

CLEAR    END

MEASUREMENT SETTING SCREEN IMAGE

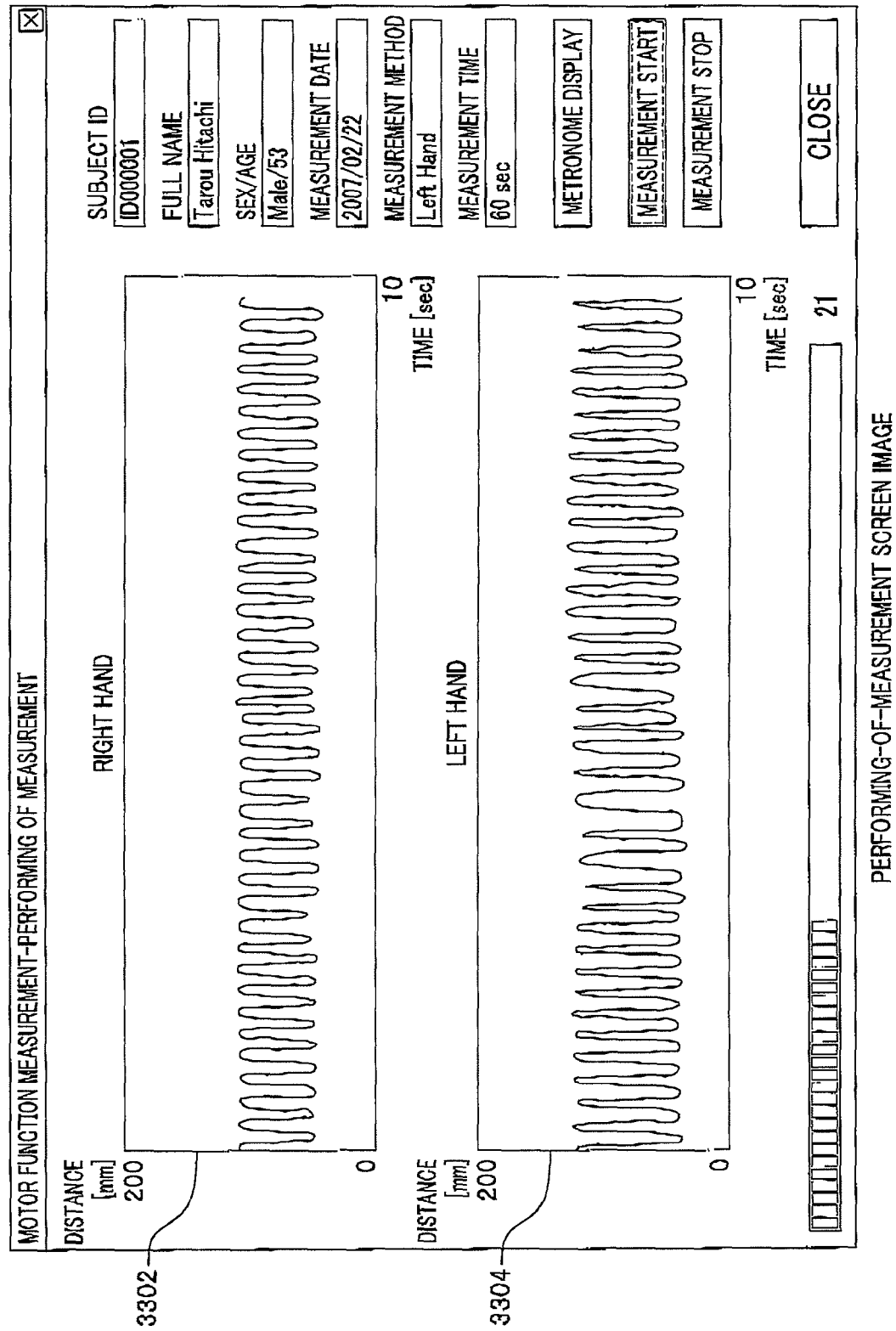

PERFORMING OF MEASUREMENT (METRONOME)

OPTION SCREEN IMAGE (MEASUREMENT SETTING TAB)

OPTION SCREEN IMAGE (PERFORMING OF MEASUREMENT TAB)

MOTOR FUNCTION MEASURING SENSOR, MOTOR FUNCTION MEASURING APPARATUS, AND MOTOR FUNCTION ANALYZING APPARATUS

CLAIM OF PRIORITY

The present application claims priority from Japanese application JP 2007-094512A filed on Mar. 30, 2007, the content of which is hereby incorporated by reference into this application.

BACKGROUND OF THE INVENTION

1. Field of the Invention

The present invention relates to a motor function measuring sensor for detecting motion of a living body, a motor function measuring apparatus for measuring a motor function of a living body, and a motor function analyzing apparatus for analyzing measurement results of the motor function measuring apparatus.

2. Description of the Related Art

Parkinson's disease is an intractable disease where a failure occurs in the sabstantia nigra or corpus striatum in a brain that controls motion of the body, thus causing ataxia in involuntary motion such as walking. Also, it is said that since being a progressive disease, if left untreated, the Parkinson's disease will become bedridden in about 10 years. Hence, early diagnosis and medical treatment are required.

U.S. Patent Application Publication No. 2005/0065422A1 discloses a living body inspection apparatus capable of detecting the motion of parts of a living body with use of a coil generating a magnetic field (refer to Japanese Patent No. 3841075, FIG. 1).

SUMMARY OF THE INVENTION

Preferably, the present invention provides a sensor for measuring motor function, a motor function measuring apparatus, and a motor function analyzing apparatus which are convenient to use.

Preferably, the present invention provides a first holder attached to a first predetermined part of the living body and a second holder attached to a second predetermined part of the living body different from the first predetermined part for the first holder are provided, and the first holder and the second holder each have an attachment surface to which to attach sticking part for detachably attaching the holder to a predetermined part of the living body. The first and second holders can be easily attached to the predetermined parts of the living body. Thus, the sensor and apparatuses are convenient to use.

BRIEF DESCRIPTION OF THE DRAWINGS

For a more complete understanding of the present invention and the advantages thereof, reference is now made to the following description taken in conjunction with the accompanying drawings wherein:

FIG. 5 is a perspective view showing a state where adhesive sheets to attach the motion sensor are arranged in a line;

FIG. 27 shows an example of a list screen image of measurement data;

FIG. 28 shows an example of a list screen image of subject data;

FIG. 29 shows an example of a subject information setting screen image;

FIG. 30 shows an example of a measurement setting screen image;

FIG. 33 shows an example of a performing-of-measurement screen image;

DETAILED DESCRIPTION OF THE INVENTION

With reference to the drawings will be described an embodiment of the invention in detail below.

Figure 1:
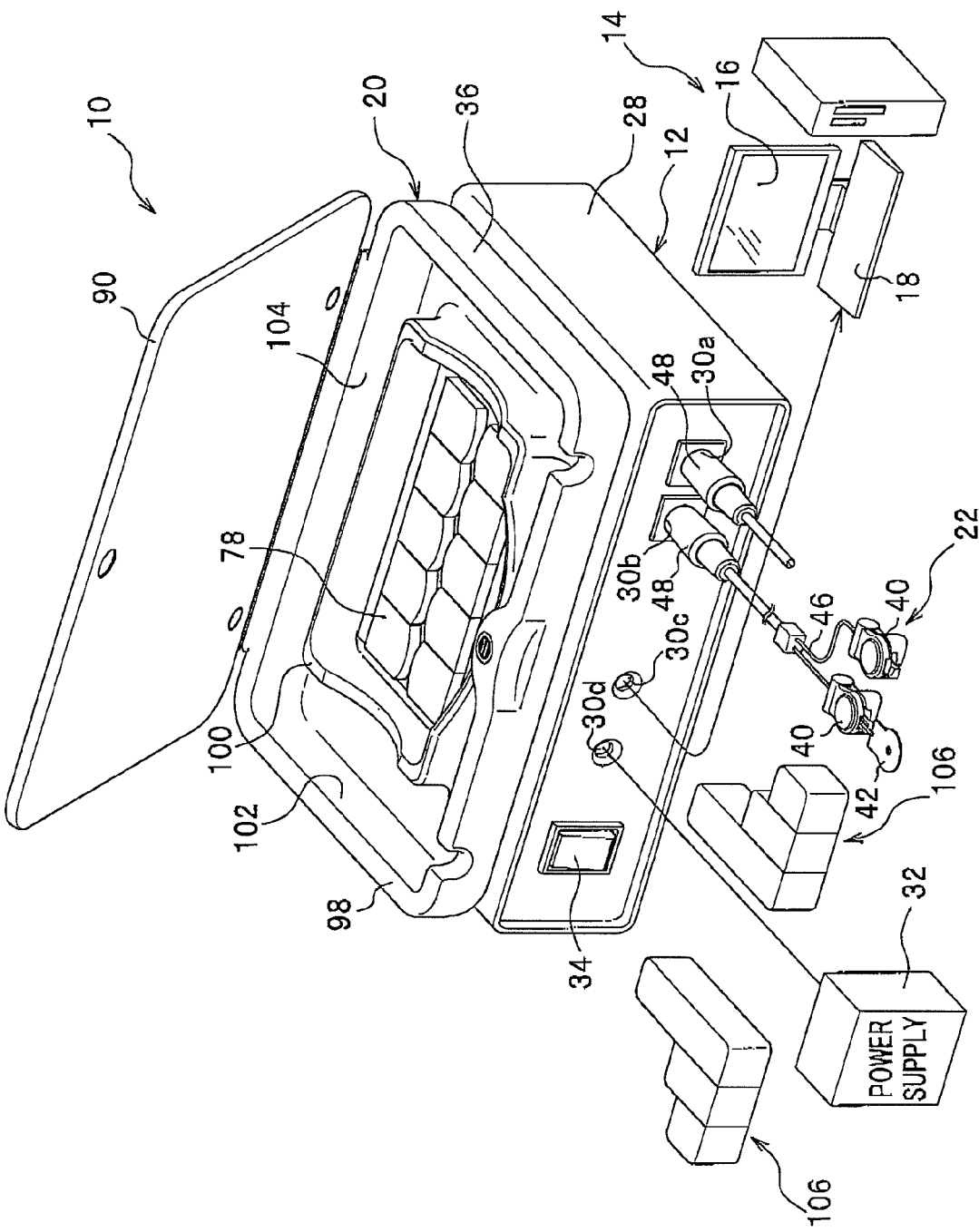
FIG. 1 is a schematic perspective view of a motor function measuring system according to an embodiment.
Figure 2:
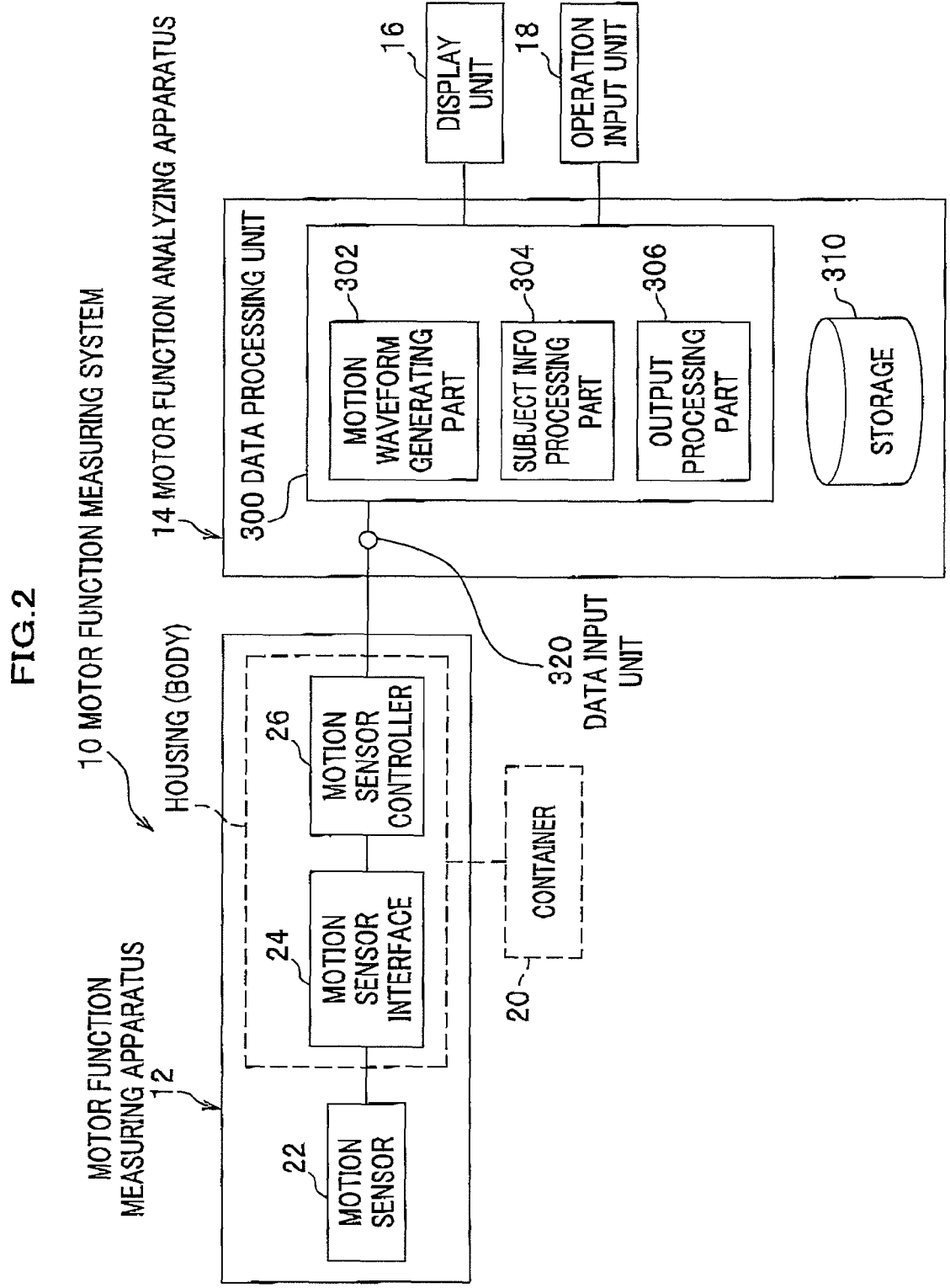
FIG. 2 is a block diagram showing the entire configuration of the motor function measuring system according to the embodiment.

FIG. 1 is a schematic perspective view of a motor function measuring system including a motor function measuring apparatus according to the present embodiment. FIG. 2 is a block diagram showing the entire configuration of the motor function measuring system.

As shown in FIGS. 1 and 2, a motor function measuring system 10 comprises a motor function measuring apparatus 12 for measuring the motion of fingers of a subject, a motor function analyzing apparatus 14 for storing and analyzing data measured by the motor function measuring apparatus 12, a display unit 16 for displaying the measurement results and the analysis results output from the apparatuses, an input unit 18 for inputting information about the subject and the like, and an containing unit 20 for containing various measuring instruments described later.

In the embodiments of the present invention, the subject as an object to be measured by the motor function measuring apparatus 12 is a living body such as an animal, and a human. The motor function measuring system 10 is for measuring motor function while having a subject quickly tapping. The motor function measuring system 10 measures motion of the fingers while the subject is tapping the index finger on the thumb as quickly as possible in response to an instruction.

[Motor Function Measuring Apparatus]

The motor function measuring apparatus 12 is for detecting motion information of the subject in a time sequence to obtain motion information of the subject concerning at least one of distance, speed, acceleration, and jerk in form of waveform data.

The motor function measuring apparatus 12 comprises a motion sensor 22 including a transmitting coil that transmits a magnetic field (magnetic field generating unit) and a receiving coil that receives the magnetic field (magnetic field detecting unit), a motion sensor interface 24, and a motion sensor controller 26. The motion sensor 22 functions as a sensor for measuring motor function.

In this case, as shown in FIG. 1, the motion sensor controller 26 is provided on a substrate (not shown) in a box-shaped housing 28 functioning as a main body. The motion sensor 22 is detachably attached to the housing 28 via a first connector 30a or a second connector 30b arranged on the front of the housing 28. As described later, the transmitting coil is attached to the top of the nail of the thumb of the subject, and the receiving coil is attached to the top of the nail of the index finger of the subject.

As shown in FIG. 1, arranged horizontally on the front panel of the housing 28 are the first and second connectors 30a, 30b connected to the motion sensors 22 for the right and left hands, a third connector 30c connected to a lead line for supplying an output signal of the motion sensor controller 26 to the motor function analyzing apparatus 14, a fourth connector 30d connected to a power supply 32 for operating the motion sensor controller 26, a switch 34 for switching on and off the motion sensor controller 26. The first to fourth connectors 30a to 30d may be arranged on the back or side of the housing 28.

In this case, the first to fourth connectors 30a to 30d may be each a female connector. A casing 36 forming the containing unit 20 is mounted on the top of the housing 28. In FIG. 1, the housing 28 having the motion sensor controller 26 therein and the casing 36 of the containing unit 20 are provided as separate units.

Figure 3:
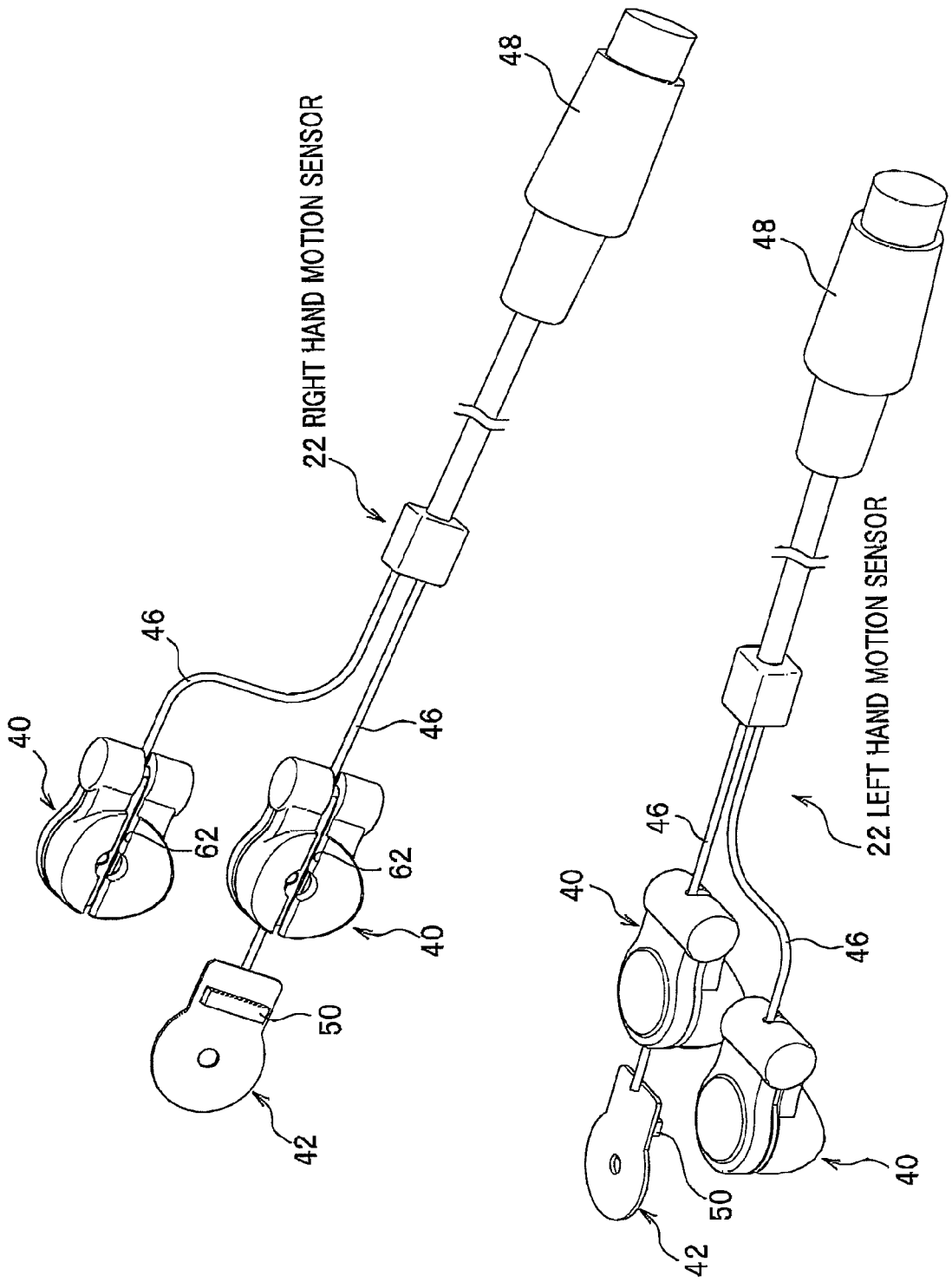
FIG. 3 is a perspective view of motion sensors for the right and left hands.

FIG. 3 is a perspective view of the motion sensors 22 for the right and left hands. As shown in FIG. 3, the motion sensors 22 are a pair of motion sensors 22 for the right and left hands that have the same configuration. Hereinafter, description will be made based on the motion sensor 22 for the left hand, whereas description of the other motion sensor 22 for the right hand is omitted.

Figure 4:
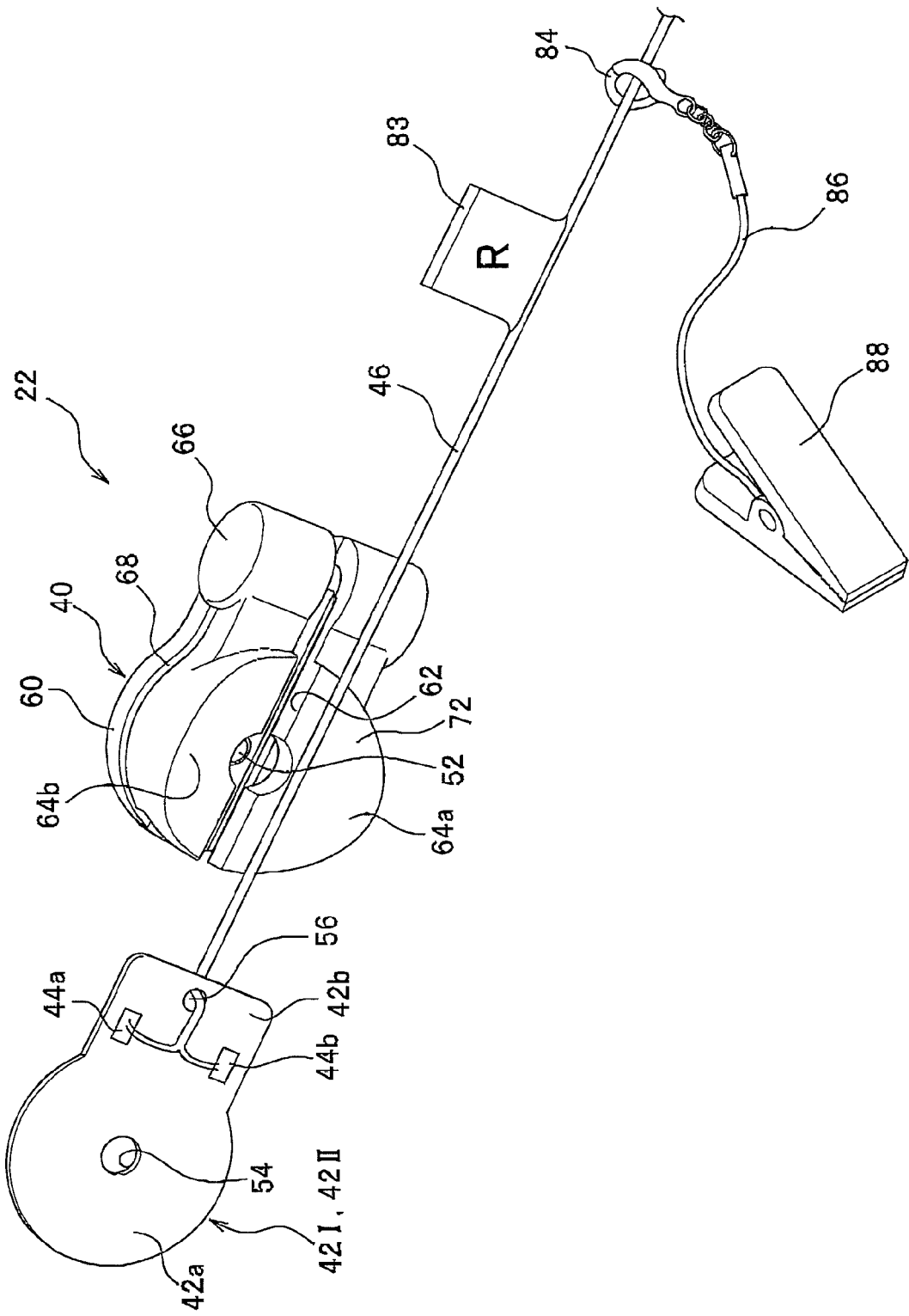
FIG. 4 is an exploded perspective view of the main part of an example of the motion sensor.
Figure 6A:
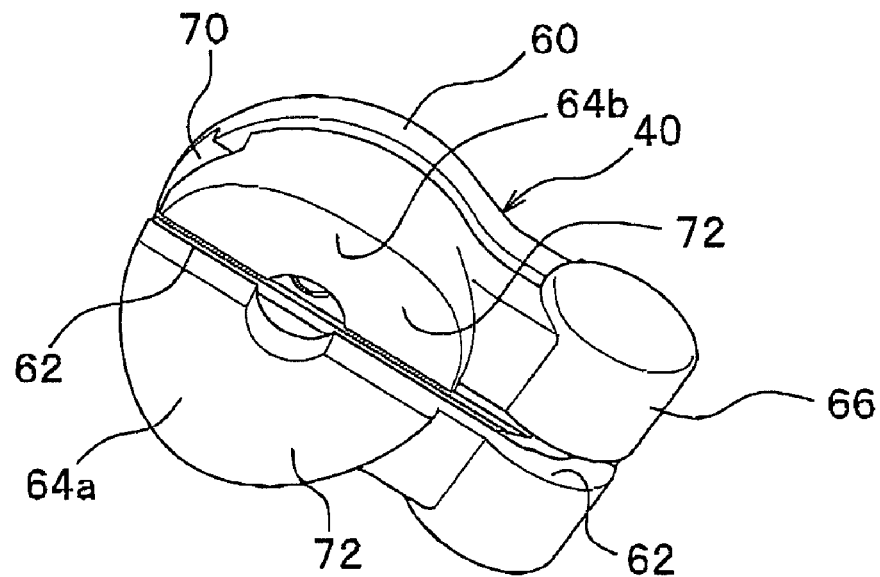
FIGS. 6A and 6B are perspective views of a holder.
Figure 6B:
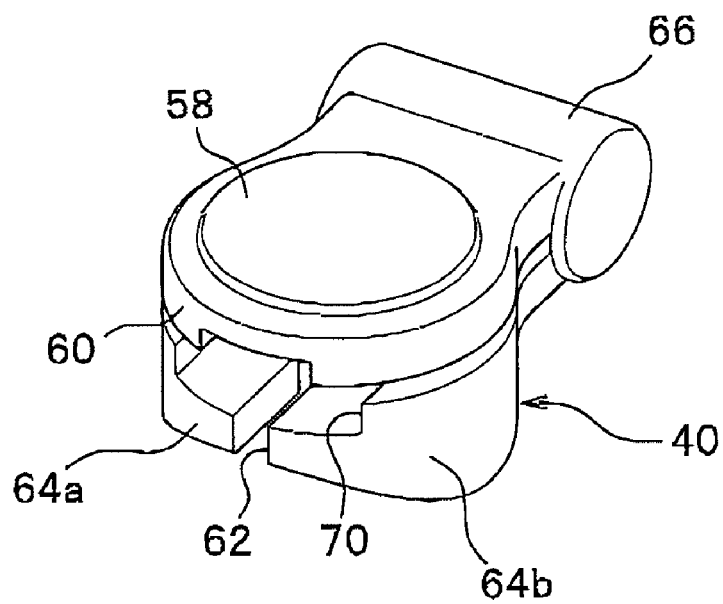
Figure 7A:
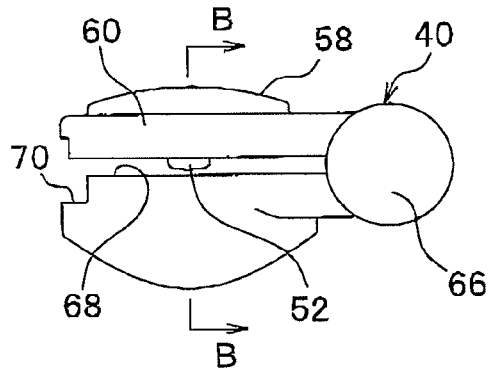
FIGS. 7A, 7B, 7C, 7D, 7E, and 7F are respectively a front view, a back view, a plan view, a bottom view, a right side view, and a left side view of the holder.
Figure 7B:
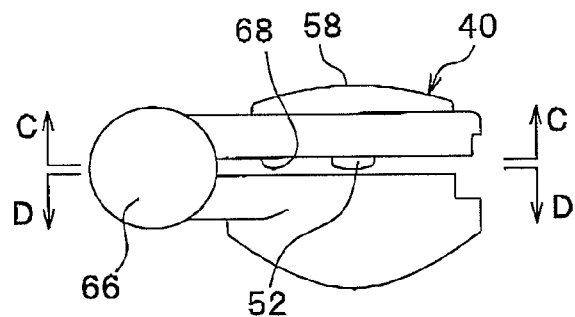
Figure 7C:
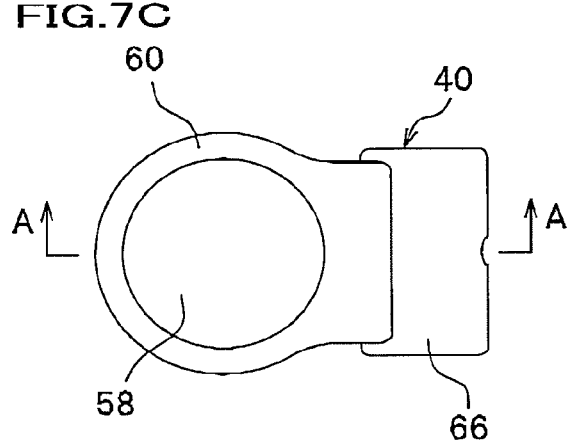
Figure 7D:
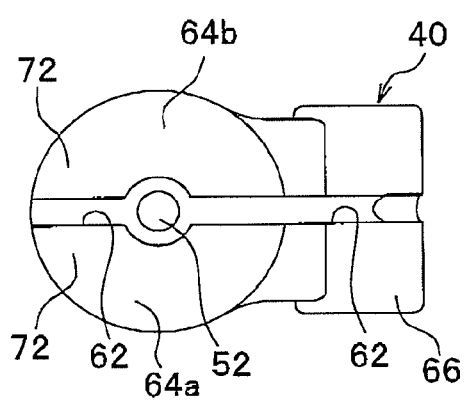
Figure 7E:
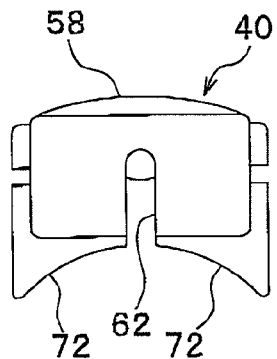
Figure 7F:
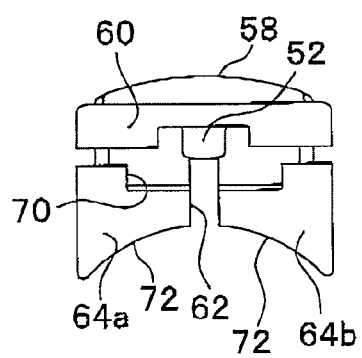
Figure 8A:
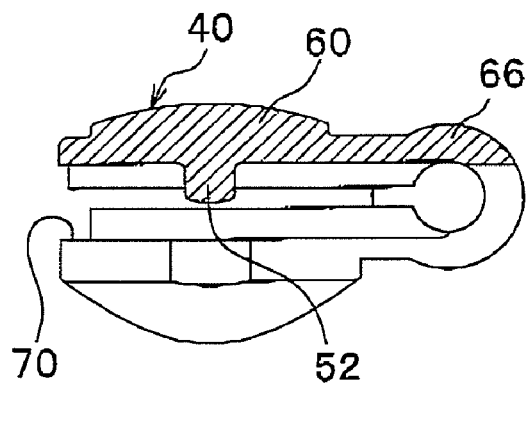
FIG. 8A is a longitudinal sectional view taken along line A-A.
Figure 8B:
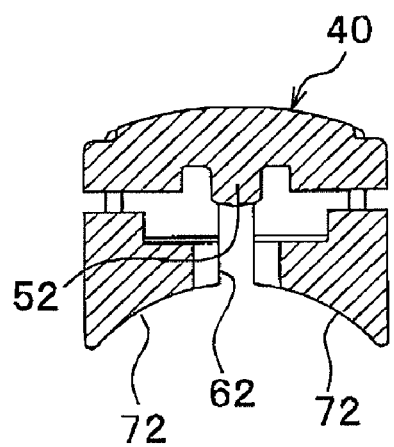
FIG. 8B is a longitudinal sectional view taken along line B-B.
Figure 8C:
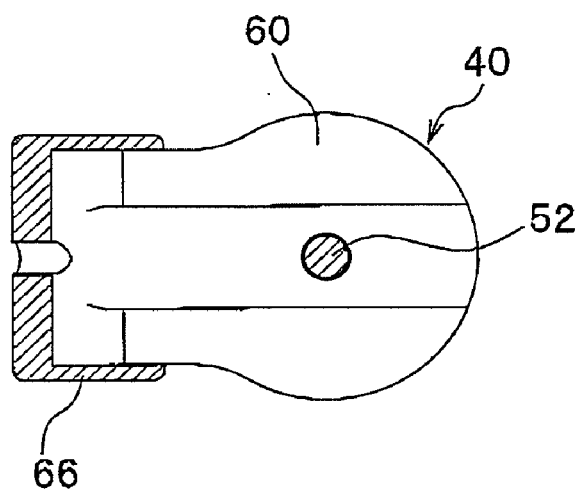
FIG. 8C is a transverse sectional view taken along line C-C.
Figure 8D:
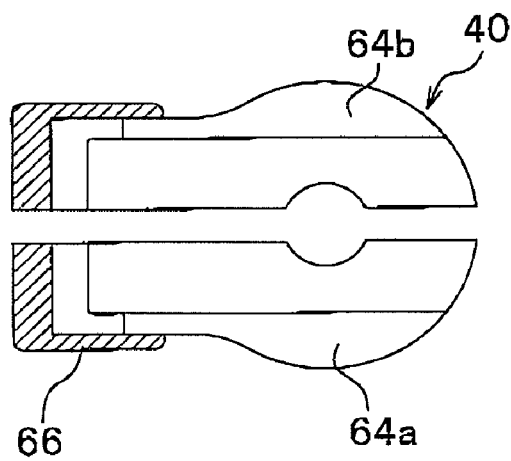
FIG. 8D is a transverse sectional view taken along line D-D.

FIG. 4 is an exploded perspective view of the main part of an example of the motion sensor 22. FIG. 5 shows that adhesive sheets 38 to stick the motion sensor 22 to the nail of a finger are arranged in parallel to each other. FIG. 6A is a perspective view showing the front, bottom, and left side of a holder 40 forming part of the motion sensor 22. FIG. 6B is a perspective view showing the front, top, and left side of the holder 40 forming part of the motion sensor 22. FIG. 7A is a front view of the holder 40, FIG. 7B is a back view of the holder 40, FIG. 7C is a plan view of the holder 40, FIG. 7D is a bottom view of the holder 40, FIG. 7E is a right side view of the holder 40, and FIG. 7F is a left side view of the holder 40. FIG. 8A is a longitudinal sectional view taken along line A-A of FIG. 7C, FIG. 8B is a longitudinal sectional view taken along line B-B of FIG. 7A, FIG. 8C is a transverse sectional view taken along line C-C of FIG. 7B, and FIG. 8D is a transverse sectional view taken along line D-D of FIG. 7B.

As shown in FIGS. 1, 3, and 4, the motion sensor 22 basically comprises the holder 40 having a coil substrate 42 for transmission or reception (hereinafter referred to as a transmitting coil substrate 42I or a receiving coil substrate 42II as needed), a lead line (electric wire) 46 electrically connected to electrodes 44a, 44b of the coil substrate 42 and running out from one end of the holder 40, a connector unit 48 provided at one end of the lead line 46 and having a plurality of connector pins (not shown) that is connected to the first connector 30a or second connector 30b, and the adhesive sheet 38 as a sticking part to stick the holder 40 to a predetermined part of the subject. In FIG. 3, reference numeral 50 indicates a cover member made of non-conductive material covering the electrodes 44a, 44b.

As shown in FIG. 4, the coil substrate 42 has: a disk 42a where a plurality of, e.g. six, layers of coils not shown (the transmitting coil as a magnetic field generating unit or the receiving coil as a magnetic field detecting unit) are pilled up one on top of another; and a substantially rectangular portion 42b formed integrally. Formed in the center of the disk 42a is a circular positioning hole 54 to engage a positioning protrusion 52 formed inside the holder 40, thereby positioning the coil substrate 42 in a predetermined position relative to the holder 40.

The pair of electrodes 44a, 44b electrically connected to both ends of the coil (not shown) is provided on the rectangular portion 42b, and the lead line 46 is electrically connected to the electrodes 44a, 44b. A small opening 56 is formed near the electrodes 44a, 44b, and the lead line 46 is made to run through the opening 56, thereby preventing the lead line 46 from being cut or detached from the electrodes.

In other words, in a comparative example (not shown) where the lead line 46 connected at one end to the electrodes 44a, 44b runs out from one end of the holder 40 without running through an opening, if the lead line 46 is pulled by some reason, the lead line 46 itself may be cut, or the end of the lead line 46 may be detached from the electrodes 44a, 44b. In contrast, in this embodiment, because the lead line 46 is made to run through the opening 56 formed in the coil substrate 42, the opening 56 prevents a force pulling the lead line 46 from being directly applied to the end of the lead line 46 by functioning as a buffer or suppressor, thereby preventing the lead line 46 from being cut or detached from the electrodes 44a, 44b. Therefore, the endurance of the lead line 46 is improved.

By providing the coil substrate 42 with an LC resonant circuit (described later) using an inductance (L) and a capacitor (C), the piled coils can be made smaller. Moreover, by setting the resonance frequency to be different between the motion sensors 22 for the right and left hands, interference can be prevented.

As shown in FIG. 3, there are a holder 40 as a first holder that is attached to the nail of a finger such as the thumb and a holder 40 as a second holder that is attached to the nail of another finger such as the index finger, and the pair of holders 40 have the same configuration.

As shown in FIGS. 7A to 7F, the holder 40 comprises an upper holder 60 having a substantially circular convex 58 on its top; first and second lower holders 64a, 64b divided in a lateral direction orthogonal to the axis according to a narrow slit 62 as a boundary extending from one end to the other end of the holder 40 along its axis; and a substantially cylindrical joint 66 coupling the upper holder 60 and the first and second lower holders 64a, 64b.

The holder 40 comprising the upper holder 60, the first and second lower holders 64a, 64b, and the joint 66 may be formed of flexible members such as resin. In this case, the upper holder 60 and first and second lower holders 64a, 64b formed separately may be bonded to the joint 66, or the upper holder 60, the first and second lower holders 64a, 64b, and the joint 66 are integrally made of resin into the holder 40.

Between the upper holder 60 and the first and second lower holders 64a, 64b, there is provided a space 68 extending horizontally in the shape corresponding to that of the coil substrate 42 in plan view (see FIGS. 7A and 7B). The coil substrate 42 is inserted into the space 68 through the opening 70 formed at one end of the holder 40 in the way that its rectangular portion 42b is at the head, and the end of the rectangular portion 42b comes into contact with the inner wall of the joint 66, and thereby the further insertion of the coil substrate 42 is stopped.

At this time, the positioning hole 54 of the coil substrate 42 comes to a position corresponding to the positioning protrusion 52 formed on the inner wall of the upper holder 60, and by pushing the upper holder 60 and first and second lower holders 64a, 64b made of flexible material against each other, the positioning protrusion 52 of the upper holder 60 engages with the positioning hole 54 of the coil substrate 42, and the coil substrate 42 is held in a predetermined position in the holder 40.

The undersides of the first and second lower holders 64a, 64b form respective curved surfaces 72 with the slit 62 in between. The curved surfaces 72 function as attachment surfaces to which sticking parts are attached. As shown in FIG. 7D, each of the curved surfaces 72 is substantially semicircular in bottom view. Meanwhile, as shown in FIGS. 7E and 7F, the curved surface 72 is formed in the shape of an arc having a predetermined curvature in side view. Because of the presence of the slit 62 between the curved surfaces 72 of the first and second lower holders 64a, 64b, the first and second lower holders 64a, 64b each can flexibly bend in an outward direction orthogonal to the slit 62 (so as to extend the diameter) correspondingly to the surface shape of the nail of the subject or flexibly bend in an inward direction orthogonal to the slit 62 (so as to shorten the diameter) correspondingly to the surface shape of the nail of the subject.

In other words, because the attachment part of the holder 40 at which the holder is attached to a nail of a subject is the pair of curved surfaces 72 axisymmetrically arranged with the slit 62 in between, the pair of curved surfaces 72 flexibly bend in outward directions so as to extend the diameter, or conversely, flexibly bend in an inward direction so as to shorten the diameter due to the action of the slit 62.

Therefore, while the surface shape (curvature) of the nail slightly varies between individuals, the holder 40 can adapt to each individual subject. When the holder 40 is attached to the nail of a subject via the adhesive sheet 38, the subject will feel a good fit without feeling that something is wrong.

The slit 62 can also be used as a line passage along the inside of the holder 40 for the lead line 46 to be inserted through (see FIG. 4). Further, because the formation of the slit 62 reduces the bulk of the holder 40, the whole of the holder 40 becomes lighter and smaller.

Although in this embodiment description is being made on the assumption that parts to which the pair of holders 40 are attached are the nails of the thumb and the index finger, the invention is not limited to this. For example, they may be other parts of the fingers than the nails.

Moreover, the present invention is not limited to the thumb and the index finger, and the holder 40 may be attached to any finger such as the little finger. Furthermore, the present invention is not limited to the nails or the fingers of a subject, and attachable parts include regions adjacent to the fingers such as the palms. Therefore, the attachable parts for the holder 40 can be the nails, fingers, and neighboring regions of a subject.

Figure 9A:
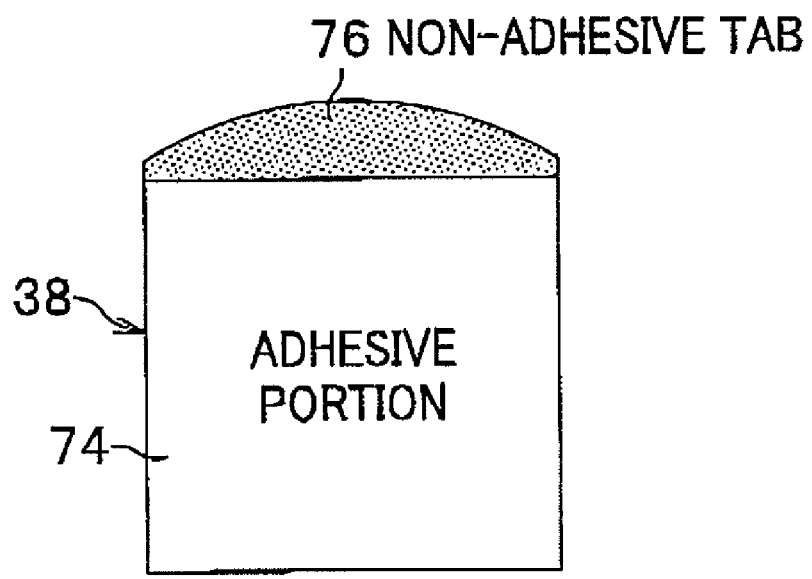
FIGS. 9A and 9B are plan views showing examples of the shape of a single adhesive sheet.
Figure 9B:
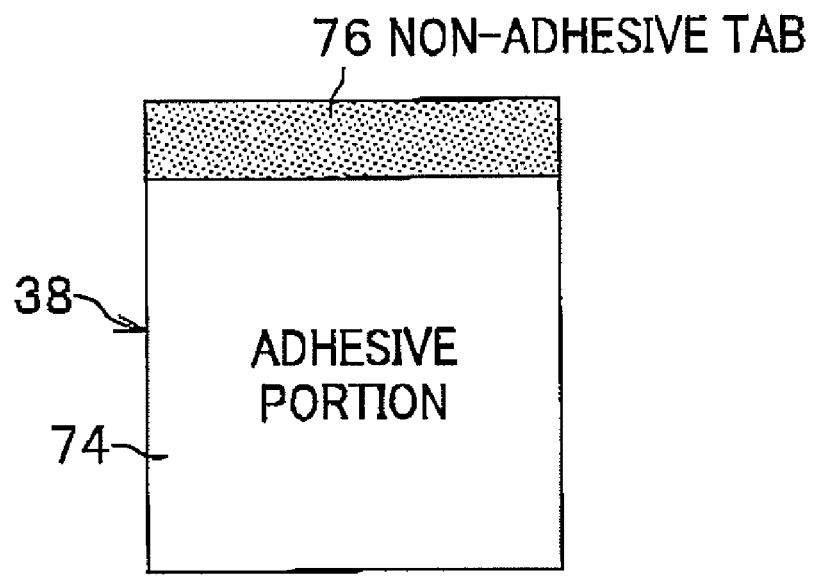

FIGS. 9A and 9B are plan views showing examples of the shape of a single adhesive sheet 38 to be attached to the nail of a subject.

This adhesive sheet 38 functions as sticking part and comprises an adhesive portion 74 having first and second adhesive surfaces provided on the front and back sides of a substantially rectangular sheet and a non-adhesive tab 76 provided at one end of the sheet having no adhesive surface, which are integrally formed. The tab 76 may be shaped like an arc as shown in FIG. 9A or rectangular as shown in FIG. 9B. Further, with the adhesive portion 74 being colorless and semi-transparent, the tab 76 may be colored so as to be distinguishable from the adhesive portion 74.

Figure 10A:
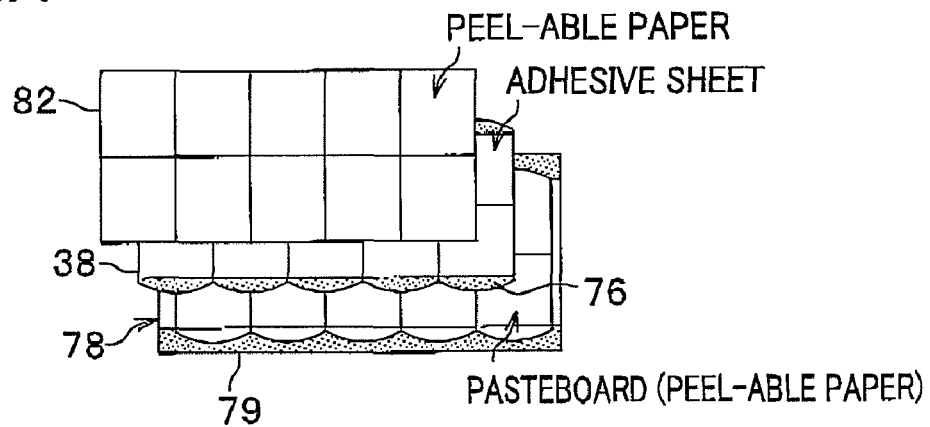
FIGS. 10A, 10B, and 10C are respectively exploded perspective views showing example configurations of an adhesive member.
Figure 10B:
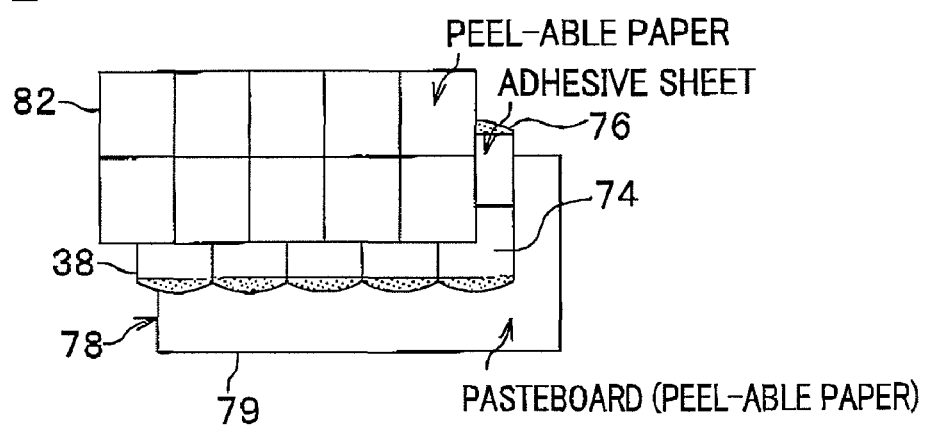
Figure 10C:
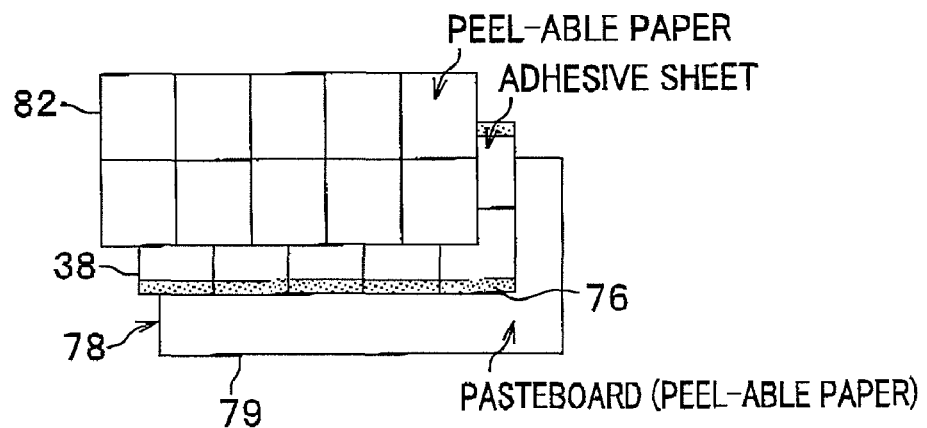
Figure 11:
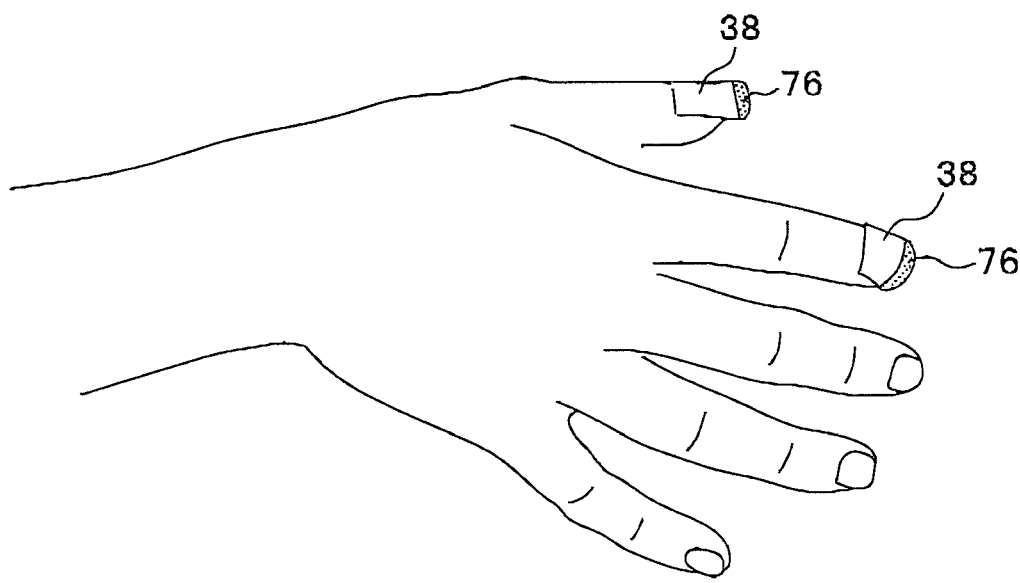
FIG. 11 is a perspective view showing the state where the adhesive sheets are stuck to nails.
Figure 12:
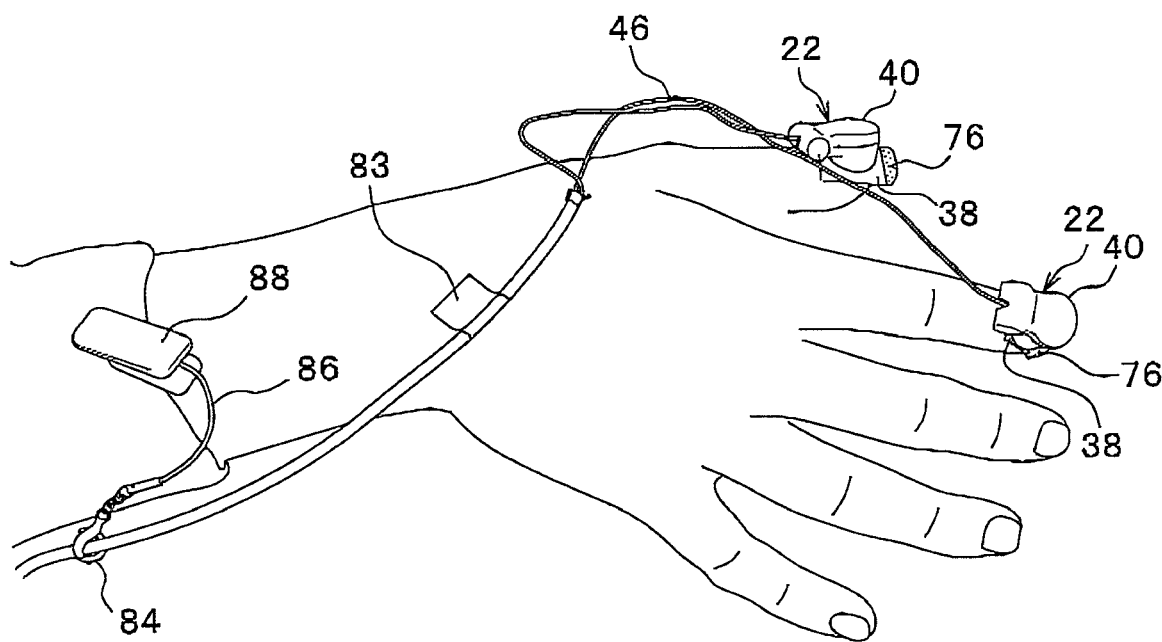
FIG. 12 is a perspective view showing the state where the holders are attached via the adhesive sheets to the nails.

FIG. 10A is an exploded perspective view showing a first example configuration of an adhesive member 78 including an adhesive sheet 38 having an arc-shaped tab 76. FIG. 10B is an exploded perspective view showing a second example configuration of the adhesive member 78 including the adhesive sheet 38 having the arc-shaped tab 76. FIG. 10C is an exploded perspective view showing a third example configuration of the adhesive member 78 including an adhesive sheet 38 having a rectangular tab 76. FIG. 11 is a perspective view showing the state where the adhesive sheets 38 are stuck to the nails of the thumb and index finger of a subject. FIG. 12 is a perspective view showing the state where the holders 40 are attached via the adhesive sheets 38 to the nails of the subject.

Figure 46A:
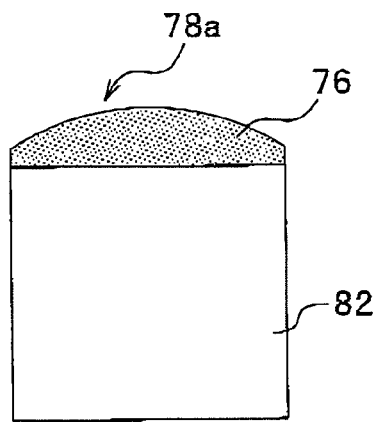
FIG. 46A is a front view of a discrete adhesive member constituted by an adhesive sheet.
Figure 46B:
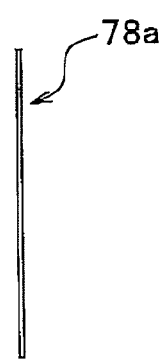
FIG. 46B is a right side view of the adhesive member.
Figure 46C:
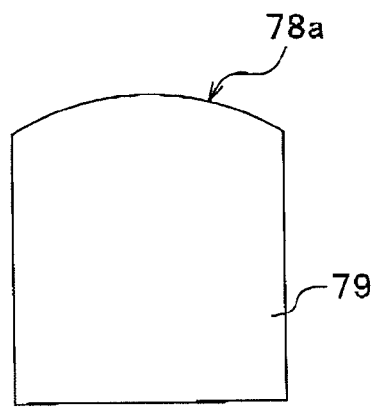
FIG. 46C is a rear view of the adhesive member.

As shown in FIGS. 10A to 10C, the adhesive member 78 comprises a pasteboard 79, the adhesive sheet 38 peel-ably mounted at the back surface thereof, that is, the second adhesive surface, on the pasteboard 79, and a peel-able body (peel-able paper) 82 mounted on the adhesive sheet 38 at the first adhesive surface, which covers only the first adhesive surface. Although the adhesive member 78 shown in FIG. 10A comprises a set of ten adhesive sheets 38, a discrete adhesive member 78a may be configured to comprise an individual adhesive sheet 38 on whose front and back surfaces are mounted a peel-able body (peel-able paper) 82 and a pasteboard (peel-able paper) 79 of the same outline as the individual adhesive sheet 38. FIG. 46 shows such a discrete adhesive member 78a; FIG. 46A is a front view of the discrete adhesive member 78a; FIG. 46B is a right side view of the discrete adhesive member 78a; and FIG. 46C is a rear view of the discrete adhesive member 78a. A left side view thereof is symmetric with the right side view.

In this case, after peeling the adhesive sheet 38 off the pasteboard 79 and sticking the adhesive sheet 38 at the back surface thereof, i.e. the second adhesive surface, to the substantially entire surface of the nail of a finger of a subject, the peel-able body 82 is peeled off the adhesive sheet 38 to make the front surface, i.e. the first adhesive surface, exposed (see FIG. 11). By pressing the curved surfaces 72 of the holder 40 having the coil substrate 42 therein against the exposed first adhesive surface of the adhesive sheet 38, the motion sensor 22 (the holders 40) is attached to the nails of the subject (see FIG. 12).

Therefore, the motion sensor 22 can be easily attached to the nails of the subject via the adhesive sheets 38, thus improving attach-ability. Further, in this embodiment, one holder 40 is attached to the nail of the thumb of a subject and the other holder 40 is attached to the nail of the index finger of the subject. Thus, even if, when measuring motion information of the subject, the thumb and the index finger of the subject cross each other and hence their inner sides cannot successfully come into contact with each other, the measurement of motion information can be achieved without a failure. Moreover, the measuring apparatus of this embodiment can be configured such that no obstruction of tapping exists on the inner sides of the thumb and the index finger when motion information of the subject is measured. As a result, the subject can smoothly perform tapping.

When being stuck to a nail of a subject, the adhesive sheet 38 may be stuck such that the non-adhesive tab 76 protrudes from the tip of the nail by a predetermined length (see FIG. 11). After measuring motion information of the subject, the subject for himself or an operator can easily peel the adhesive sheet 38 off the nail by holding the non-adhesive tab 76.

As such, in the present embodiment, the adhesive sheet 38 is interposed between the holder 40 and a nail of a subject, and after measuring motion information of the subject, the adhesive sheet 38 can be peeled off to be disposed. Hence, the motion sensor 22 need not be disinfected or cleaned, and the effect of being hygienic is obtained. In other words, by disposing the adhesive sheet 38 in direct contact with a nail after used and using a new adhesive sheet 38 in the next measurement, the holder 40 having the coil substrate 42 therein can be used any number of times.

Moreover, in the present embodiment, because the motion sensor 22 can be easily attached to a nail of a subject via the adhesive sheet 38, the convenient motor function measuring apparatus 12 can be obtained. For example, where the motor function measuring apparatus 12 according to the present embodiment is used for medical use, a doctor that is an operator need not perform troublesome work and can attach the motion sensor 22 to a patient very easily and in a short time, so that the usability of the motor function measuring apparatus 12 in medical use is improved. The motor function measuring apparatus 12 for detecting the motion of a living body can be applied to the diagnosis of, e.g., cerebral infarction, rheumatism, arthritis, and the like as well as the diagnosis of Parkinson's disease.

Figure 13A:
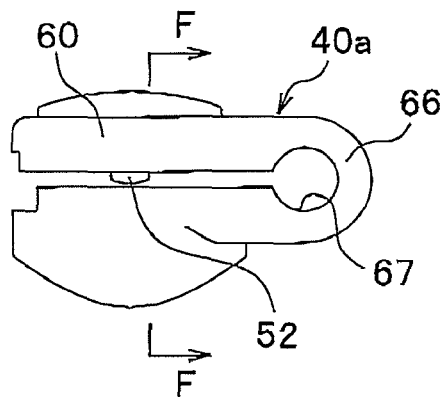
FIGS. 13A, 13B, 13C, 13D, 13E, and 13F are respectively a front view, a back view, a plan view, a bottom view, a right side view, and a left side view of a holder according to a first modification.
Figure 13B:
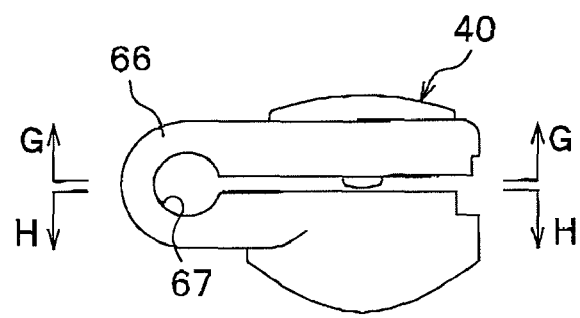
Figure 13C:
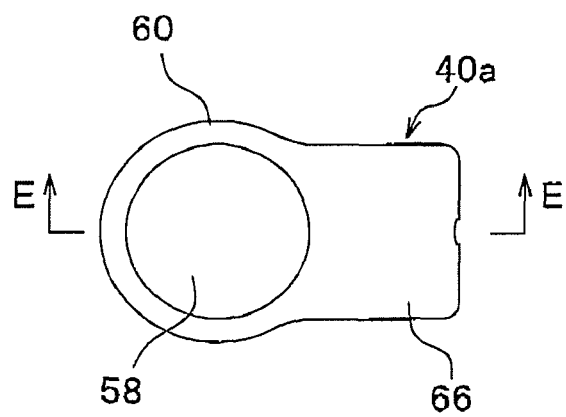
Figure 13D:
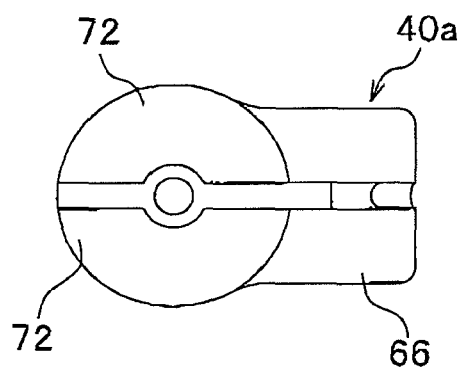
Figure 13E:
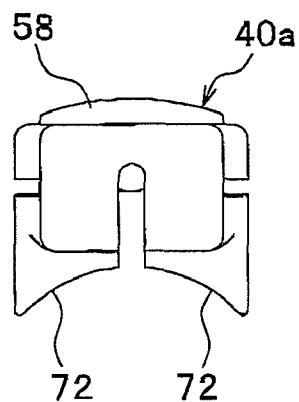
Figure 13F:
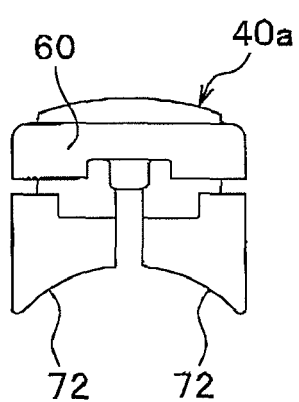
Figure 14A:
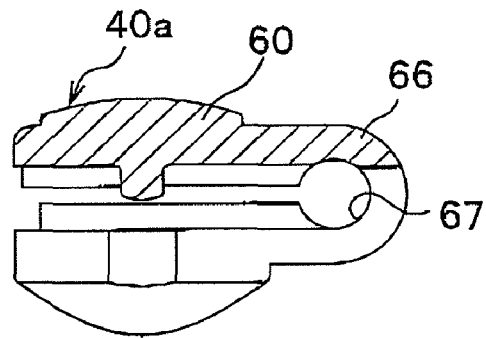
FIG. 14A is a longitudinal sectional view taken along line E-E.
Figure 14B:
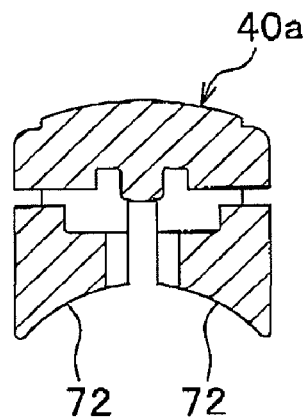
FIG. 14B is a longitudinal sectional view taken along line F-F.
Figure 14C:
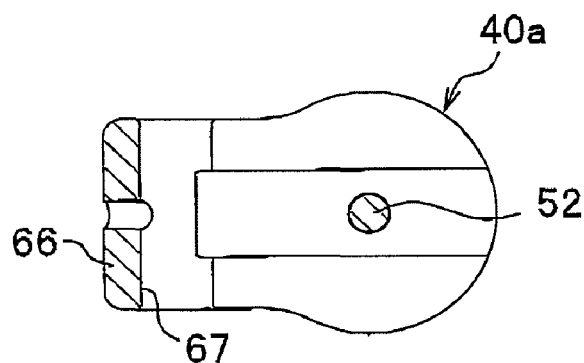
FIG. 14C is a transverse sectional view taken along line G-G.
Figure 14D:
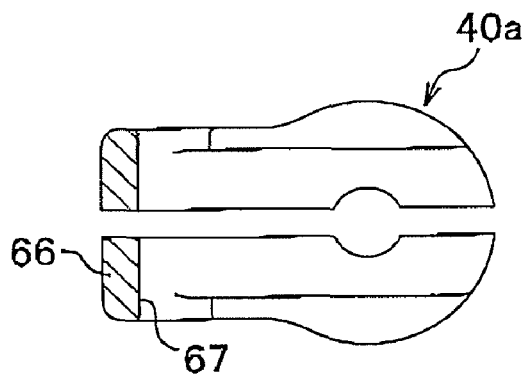
FIG. 14D is a transverse sectional view taken along line H-H.
Figure 25A:
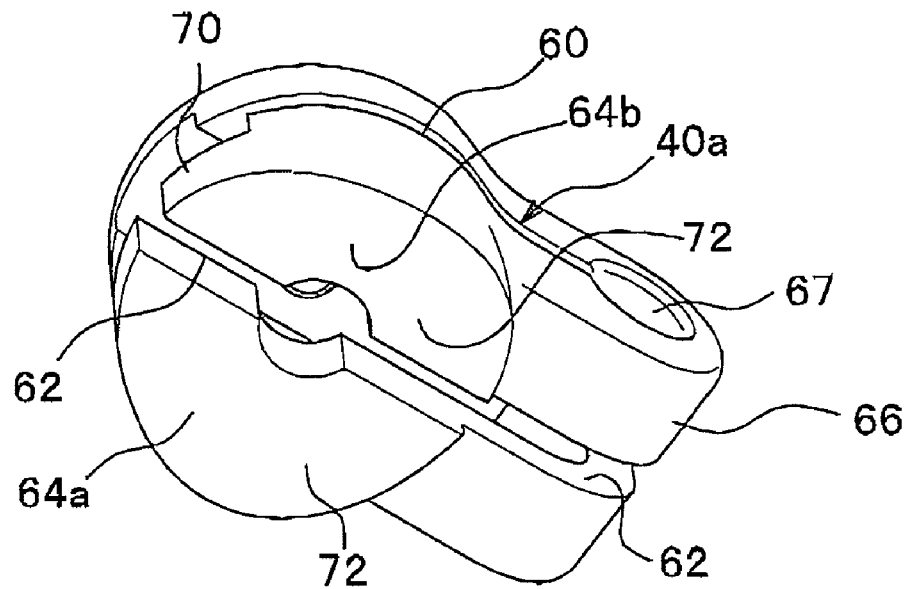
FIGS. 25A and 25B are respectively perspective views of the holder according to the first modification.
Figure 25B:
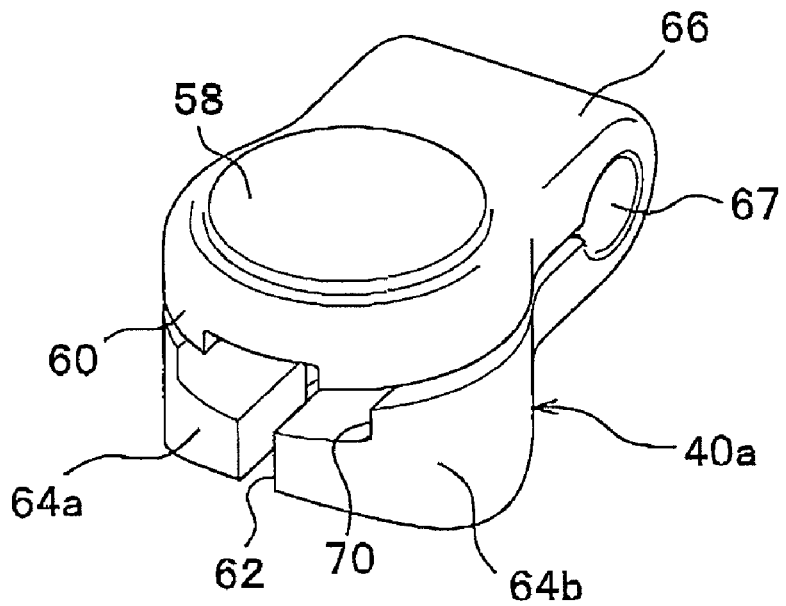

FIG. 13A is a front view of a holder 40a according to a first modification; FIG. 13B is a back view of the holder 40a; FIG. 13C is a plan view of the holder 40a; FIG. 13D is a bottom view of the holder 40a; FIG. 13E is a right side view of the holder 40a; and FIG. 13F is a left side view of the holder 40a. FIG. 14A is a longitudinal sectional view taken along line E-E of FIG. 13C, FIG. 14B is a longitudinal sectional view taken along line F-F of FIG. 13A, FIG. 14C is a transverse sectional view taken along line G-G of FIG. 13B, and FIG. 14D is a transverse sectional view taken along line H-H of FIG. 13B. FIG. 25A is a perspective view showing the front, bottom, and left side of the holder 40a according to the first modification. FIG. 25B is a perspective view showing the front, top, and left side of the holder 40a. In the holder 40a according to the first modification, a hole 67 extending through the joint 66 for the reduction of the bulk is formed, thereby making the holder 40a lighter and reducing production costs. In FIGS. 6 to 8, the same reference numerals indicate the same components as in the holder 40 of FIG. 8 with detailed description thereof being omitted.

Figure 40A:
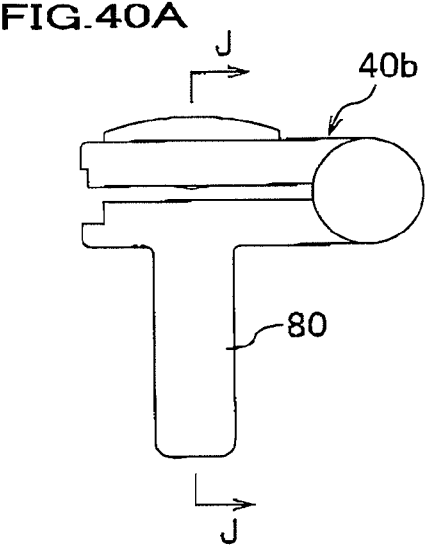
FIGS. 40A, 40B, 40C, 40D, 40E, and 40F are respectively a front view, a back view, a plan view, a bottom view, a right side view, and a left side view of a holder according to a second modification.
Figure 40B:
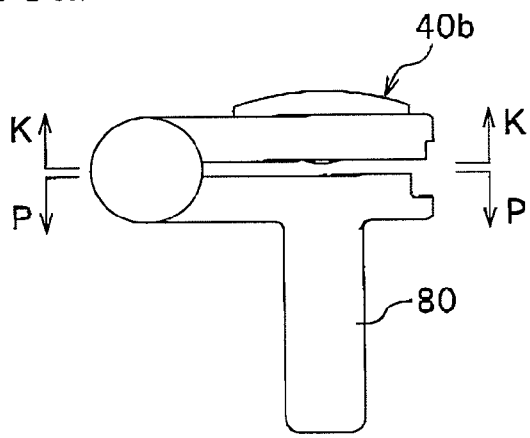
Figure 40C:
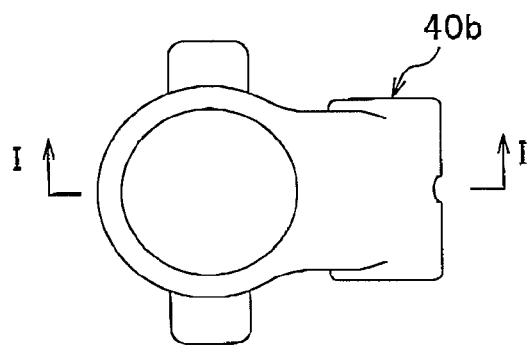
Figure 40D:
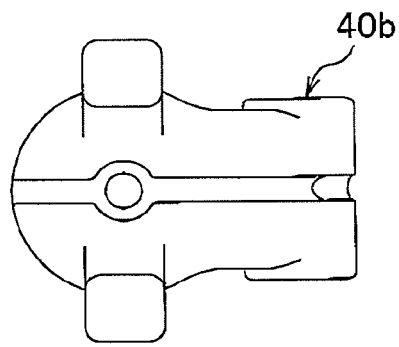
Figure 40E:
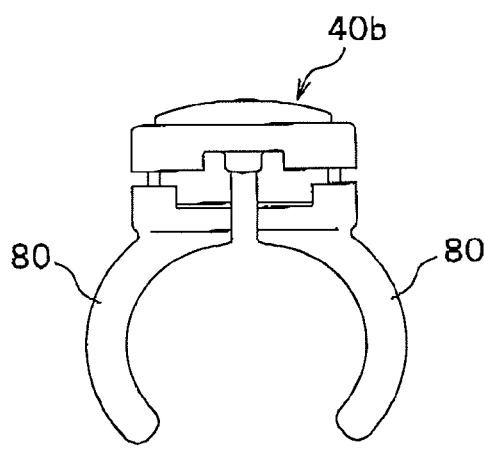
Figure 40F:
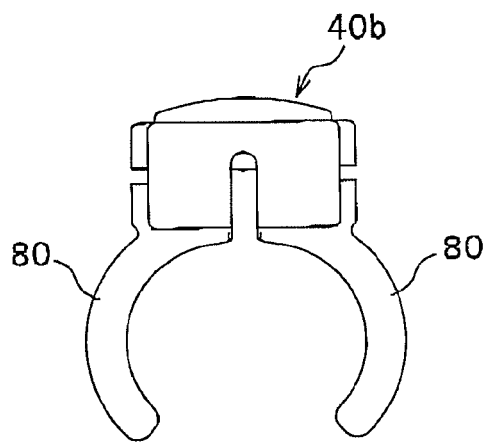
Figure 41A:
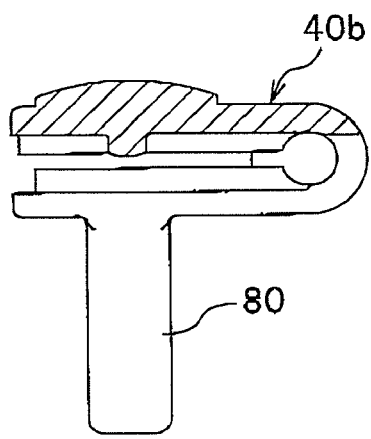
FIG. 41A is a longitudinal sectional view taken along line I-I.
Figure 41B:
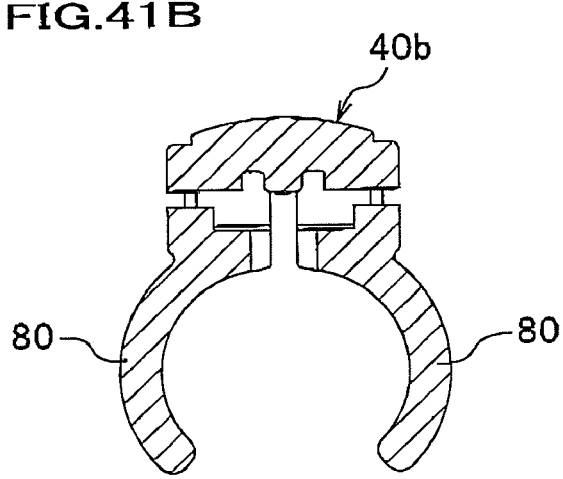
FIG. 41B is a longitudinal sectional view taken along line J-J.
Figure 41C:
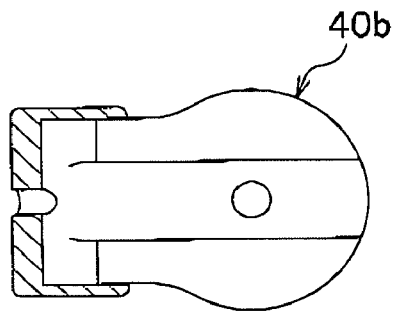
FIG. 41C is a transverse sectional view taken along line K-K.
Figure 41D:
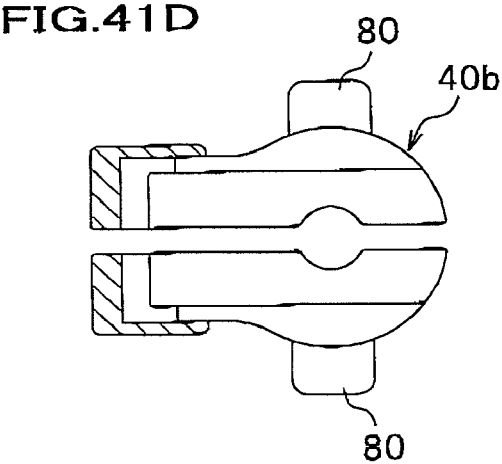
FIG. 41D is a transverse sectional view taken along line P-P.
Figure 42A:
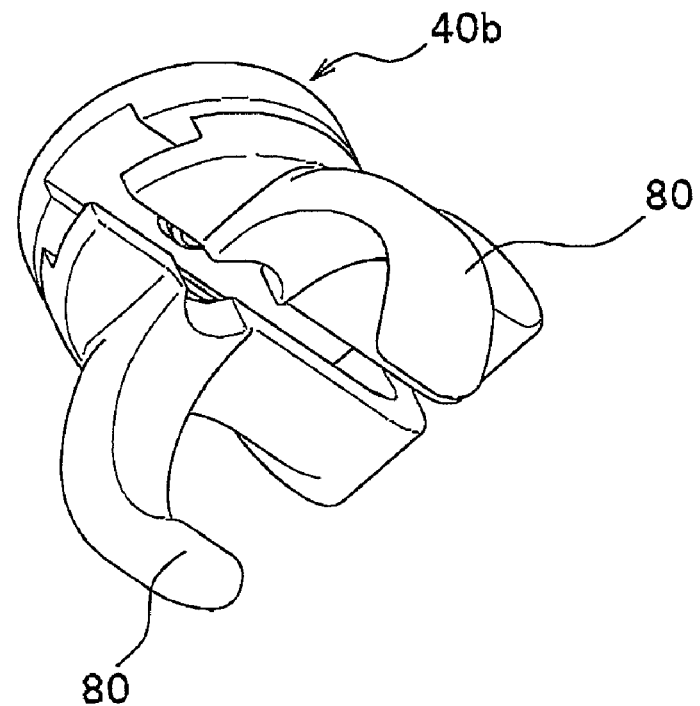
FIGS. 42A and 42B are perspective views of the holder according to the second modification.
Figure 42B:
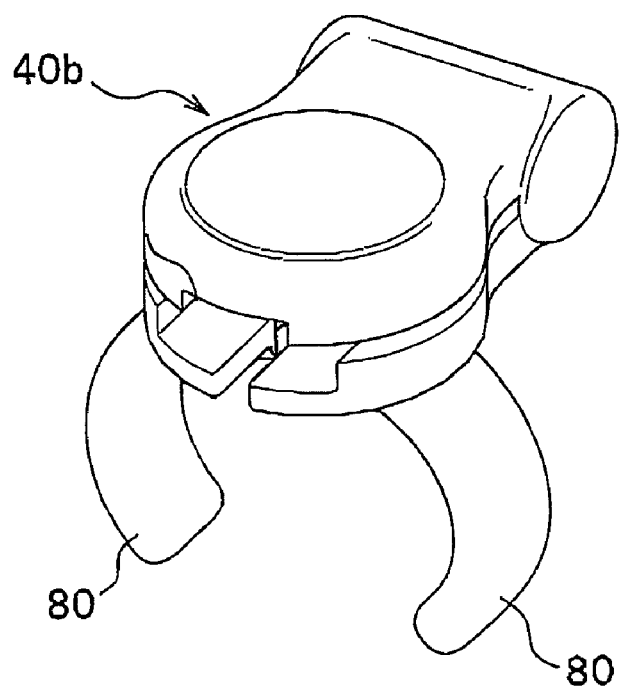

FIG. 40A is a front view of a holder 40b according to a second modification; FIG. 40B is a back view of the holder 40b; FIG. 40C is a plan view of the holder 40b; FIG. 40D is a bottom view of the holder 40b; FIG. 40E is a right side view of the holder 40b; and FIG. 40F is a left side view of the holder 40b. FIG. 41A is a longitudinal sectional view taken along line I-I of FIG. 40C, FIG. 41B is a longitudinal sectional view taken along line J-J of FIG. 40A, FIG. 41C is a transverse sectional view taken along line K-K of FIG. 40B, and FIG. 41D is a transverse sectional view taken along line P-P of FIG. 40B. FIG. 42A is a perspective view showing the front, bottom, and left side of the holder 40b according to the second modification. FIG. 42B is a perspective view showing the front, top, and left side of the holder 40b. In the holder 40b according to the second modification, a flexible C-shaped ring 80 curved substantially like a C with an opening in the middle is formed integrally with the holder 40b. By putting the C-shaped ring 80 along a fingertip of a subject into place, the holder 40b is easily attached.

Figure 43A:
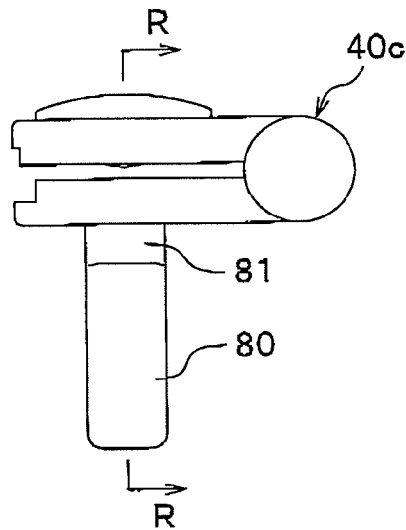
FIGS. 43A, 43B, 43C, 43D, 43E, and 43F are respectively a front view, a back view, a plan view, a bottom view, a right side view, and a left side view of a holder according to a third modification.
Figure 43B:
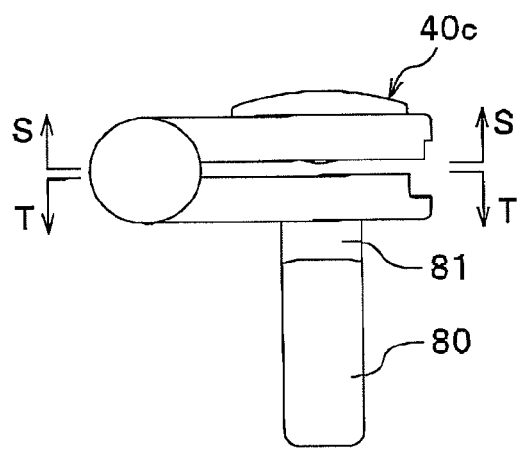
Figure 43C:
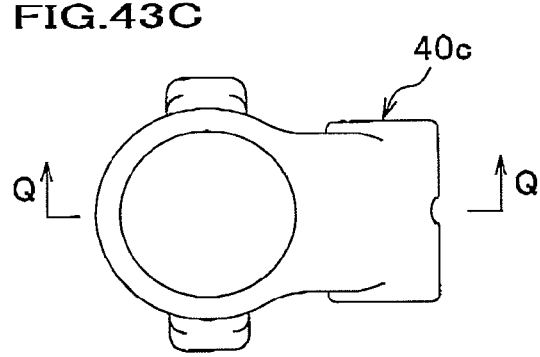
Figure 43D:
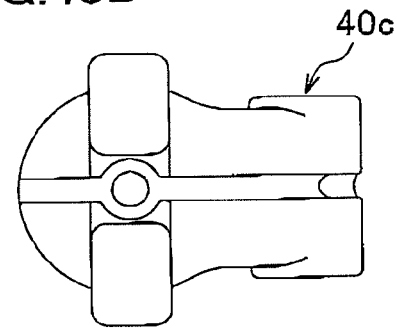
Figure 43E:
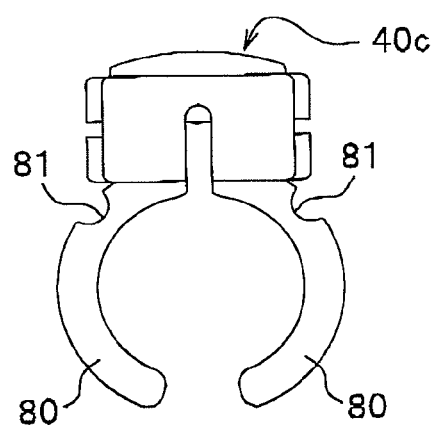
Figure 43F:
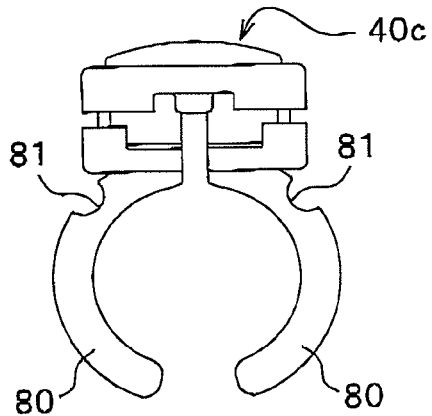
Figure 44A:
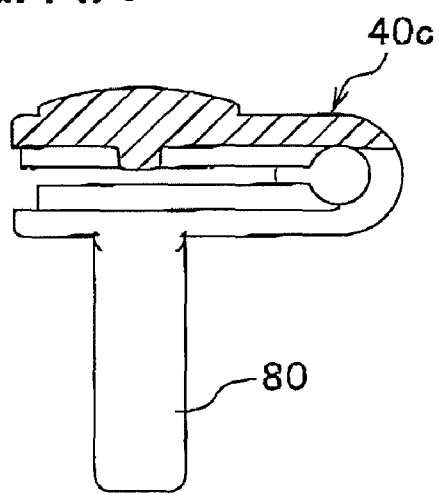
FIG. 44A is a longitudinal sectional view taken along line Q-Q.
Figure 44B:
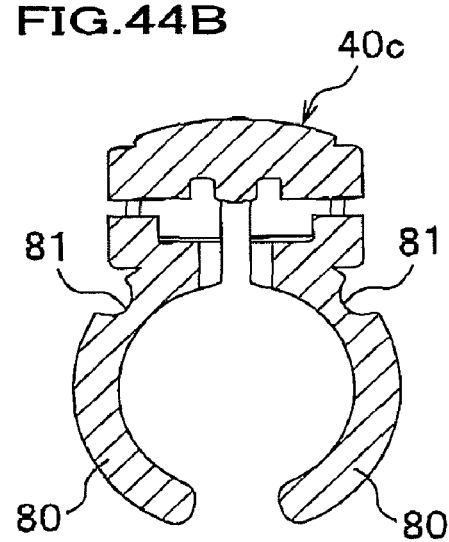
FIG. 44B is a longitudinal sectional view taken along line R-R.
Figure 44C:
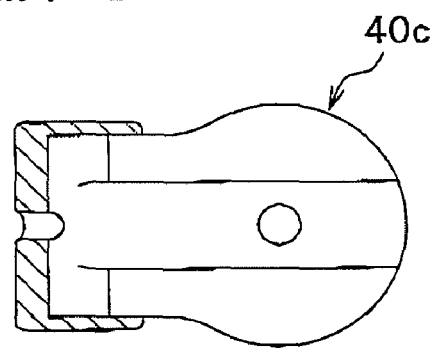
FIG. 44C is a transverse sectional view taken along line S-S.
Figure 44D:
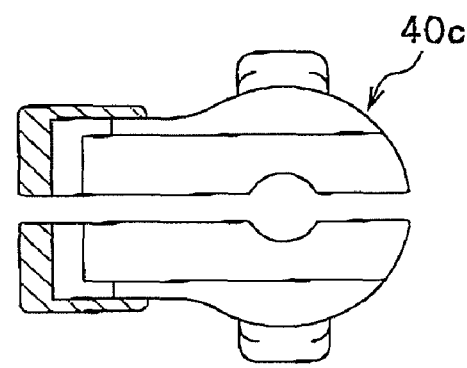
FIG. 44D is a transverse sectional view taken along line T-T.
Figure 45A:
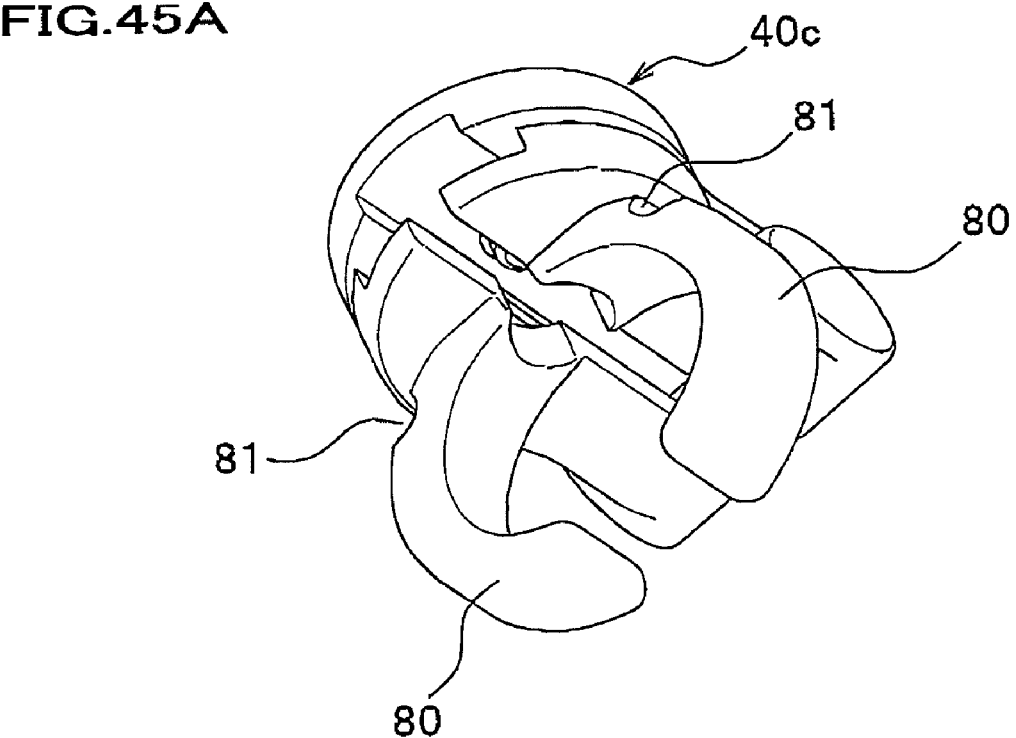
FIGS. 45A and 45B are perspective views of the holder according to the third modification.
Figure 45B:
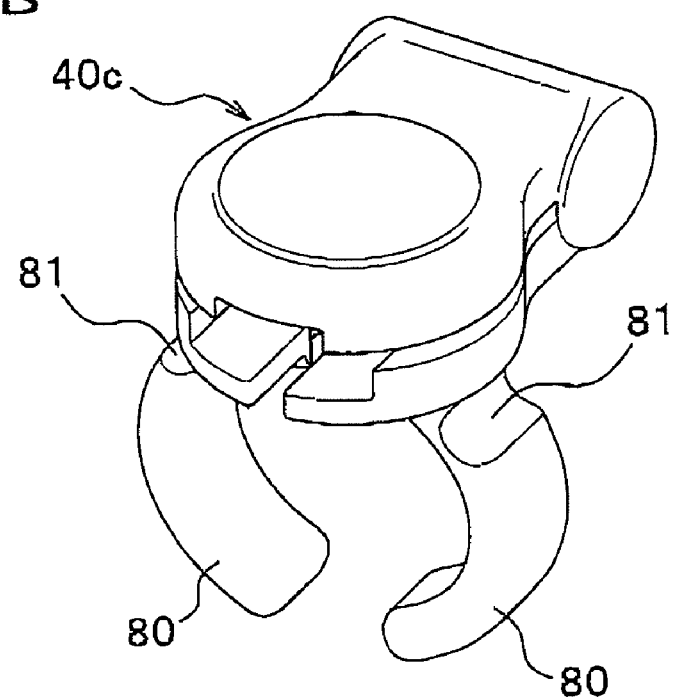

FIG. 43A is a front view of a holder 40c according to a third modification; FIG. 43B is a back view of the holder 40c; FIG. 43C is a plan view of the holder 40c; FIG. 43D is a bottom view of the holder 40c; FIG. 43E is a right side view of the holder 40c; and FIG. 43F is a left side view of the holder 40c. FIG. 44A is a longitudinal sectional view taken along line Q-Q of FIG. 43C, FIG. 44B is a longitudinal sectional view taken along line R-R of FIG. 43A, FIG. 44C is a transverse sectional view taken along line S-S of FIG. 43B, and FIG. 44D is a transverse sectional view taken along line T-T of FIG. 43B. FIG. 45A is a perspective view showing the front, bottom, and left side of the holder 40c according to the third modification. FIG. 45B is a perspective view showing the front, top, and left side of the holder 40c. In the holder 40c according to the third modification, cuts 81 of an arc-shaped cross section are made in the upper portions of a C-shaped ring 80 (see FIG. 44b), thereby making the holder further lighter, in which respect the holder 40c differs from the holder 40b according to the second modification.

As shown in FIG. 4, distinguishing part 83 having a letter R marked to indicate the motion sensor 22 being for the right hand or a letter L marked to indicate the motion sensor 22 being for the left hand is, for example, molded integrally with the tube of the lead line 46 in the middle, connected to the coil substrate 42.

The distinguishing part 83 is not limited to one molded integrally with the tube of the lead line 46. For example, an adhesive tape piece of a predetermined length or the like may be stuck to a predetermined position on the tube such that the adhesive tape piece folded in half is like a flag with the tube as a flagpole, and a symbol or a letter such as an R or L may be marked on the flag-like adhesive tape piece (see FIG. 12).

Further, the tube forming the lead line 46 may be colored differently, for example, red for the right hand and yellow for the left hand. Thus, with the distinguishing part 83 and the coloring of the tube, the subject and the operator can be reliably prevented from mistaking the right hand motion sensor 22 for the left hand motion sensor or vice versa. The colors of the tubes are not limited to red and yellow.

Yet further, the stepped cylindrical connector unit 48 (see FIG. 3) provided at one end of the lead line 46 has a plurality of connector pins (not shown) that are connected to the first connector 30a or second connector 30b. Different numbers of connector pins are provided for the right hand motion sensor 22 and the left hand motion sensor 22. For example, the number of connector pins for the right hand is five, and the number of connector pins for the left hand is four. Thus, the right hand first connector 30a and the left hand second connector 30b can be reliably prevented from being misconnected to the left hand connector unit 48 and the right hand connector unit 48.

Further, the number of the holes to be fit into the pins or a hole of size for the pin may be differentiated.

As shown in FIGS. 4 and 12, in the middle of the lead line 46, there are provided a string-like or strip-like string member 86 connected at one end to a fastener 84 engaging a predetermined place of the lead line 46 and a clip member 88 connected to the string member 86 at the other end, which can be fastened to a sleeve or the like of the outerwear of a subject. Providing the string member 86 and the clip member 88 presents the following benefits: first, by supporting the long lead line 46 in the middle, reducing the load imposed on a subject; second, restricting the extending direction of the lead line 46 to directions not going away from the subject; and third, by temporarily fastening the clip member 88 to a sleeve or the like of the outerwear of the subject beforehand, easily attaching the holder 40 to a nail.

Figure 15:
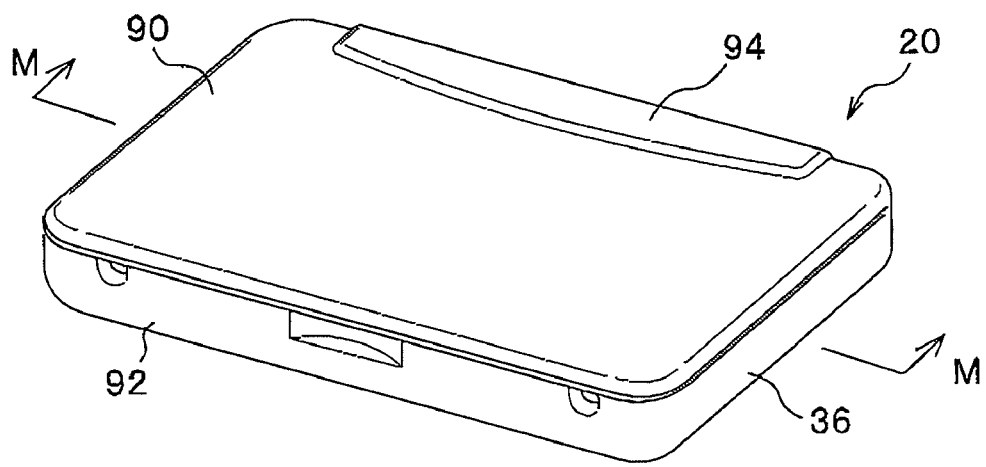
FIG. 15 is a perspective view showing the state where a cover of a casing forming part of an containing unit is closed.
Figure 16:
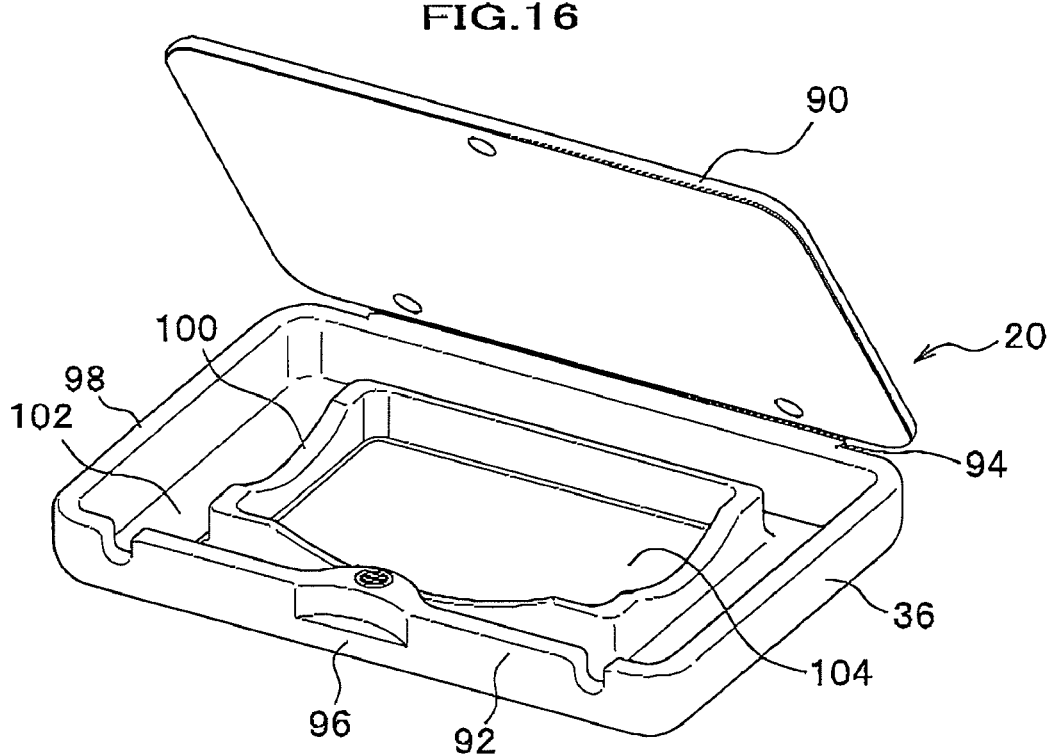
FIG. 16 is a perspective view showing the state where the cover of the casing is open.
Figure 17:
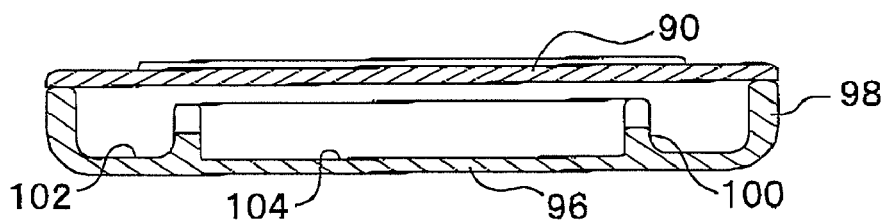
FIG. 17 is a longitudinal sectional view of the casing on line M-M.
Figure 18:
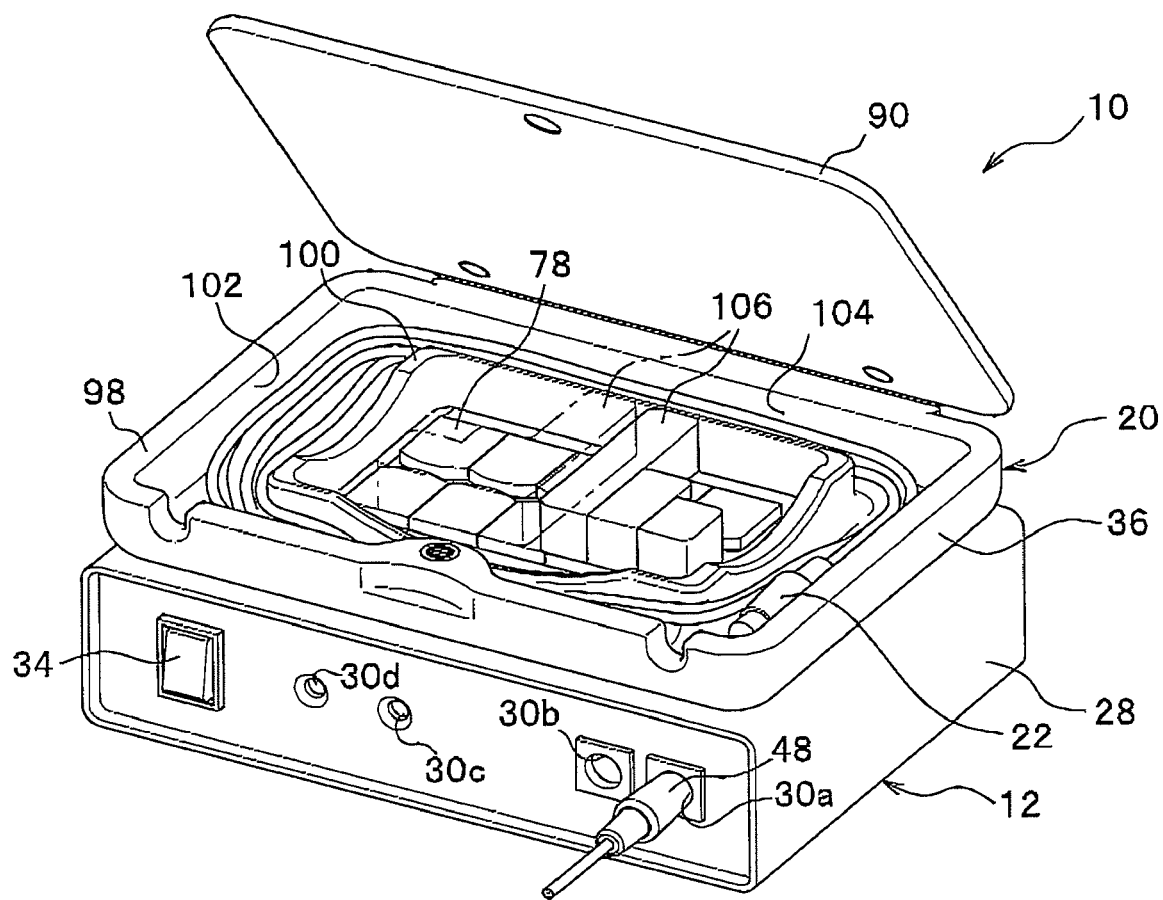
FIG. 18 is a perspective view showing a state where various measuring instruments are contained in the casing.

FIG. 15 is a perspective view showing the state where a cover 90 of the casing 36 forming part of the containing unit 20 is closed. FIG. 16 is a perspective view showing the state where the cover 90 of the casing 36 is open. FIG. 17 is a longitudinal sectional view taken along line M-M of FIG. 15. FIG. 18 is a perspective view showing the state where various measuring instruments including the motion sensor 22, etc., are contained in the casing 36.

As shown in FIG. 16, this casing 36 comprises a case body 92 shaped substantially like a cylinder having the bottom, the plate-shaped cover 90 for opening and closing the opening made in the case body 92, and a hinge 94 supporting the cover 90 in an openable and closable manner with respect to the case body 92. The case body 92, the cover 90, and the hinge 94 may be made of, e.g., a resin or a light metal such as aluminum in order to make the casing convenient, e.g., to carry and lighter.

The case body 92 comprises a bottom wall 96 constituted by a wide rectangular plate, an outer wall 98 formed along the periphery of the bottom wall 96 that forms a rectangular first frame, and an inner wall 100 formed inward of the outer wall 98 that forms a rectangular second frame. In between the outer wall 98 and the inner wall 100, there is provided a first containing space 102 in a rectangular circuit. A pair of motion sensors 22 for the right and left hands is contained along the first containing space 102.

A second containing space 104 is provided inward of the inner wall 100, and a plurality of adhesive members 78 laid one on top of another and a pair of calibration blocks 106 are arranged in the second containing space 104.

Figure 19:
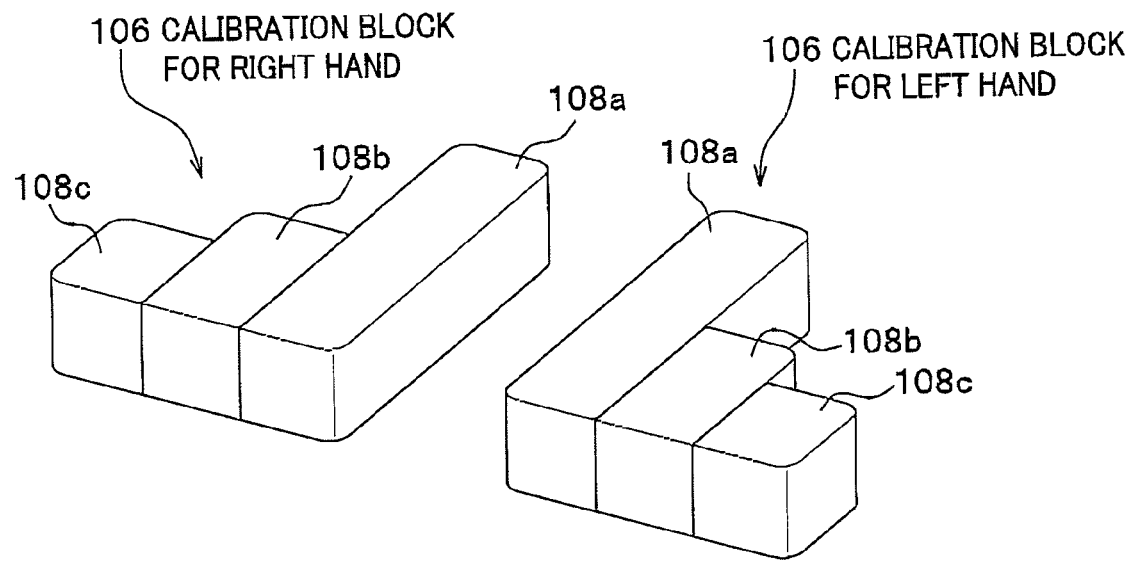
FIG. 19 is a perspective view showing an example configuration of calibration blocks.
Figure 20:
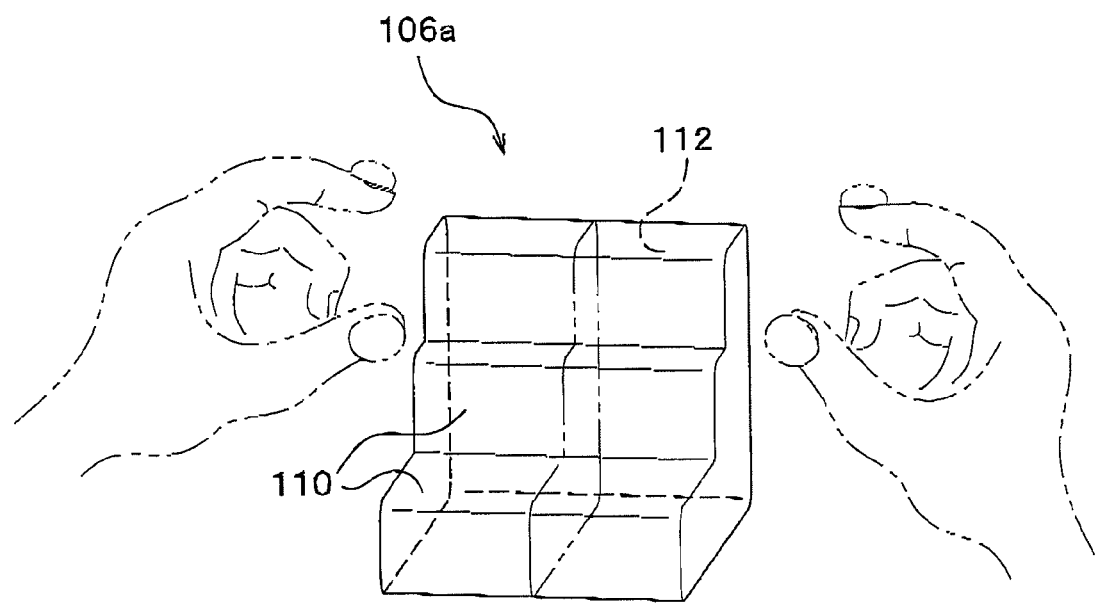
FIG. 20 is a perspective view showing another example configuration of a calibration block.
Figure 21:
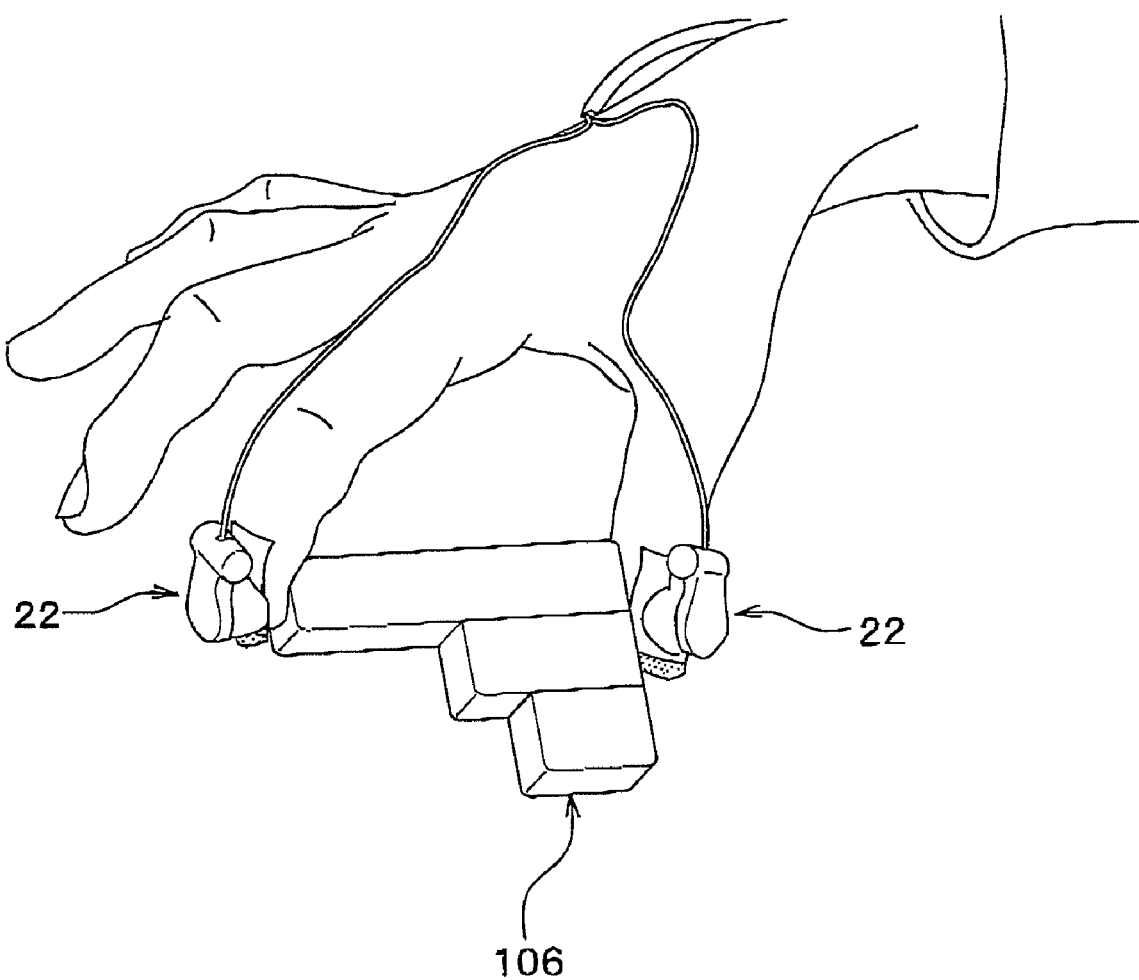
FIG. 21 is a perspective view showing a state where a subject is holding a calibration block with the thumb and the index finger.

FIG. 19 is a perspective view showing an example configuration of a pair of separate calibration blocks 106. FIG. 20 is a perspective view showing an example configuration of a single calibration block 106a integrally formed. FIG. 21 is a perspective view showing a state where a subject is holding the calibration block 106 with the thumb and the index finger.

As shown in FIG. 21, the calibration blocks 106 (106a) is an instrument used to obtain voltage information at a predetermined distance when a subject is holding the calibration block 106 (106a) with the thumb and the index finger to calibrate for the subject based on the voltage information because each subject is different in the size or the like of the fingers.

As shown in FIG. 19, there are two types of calibration blocks 106, one for the right hand and one for the left hand, each of which consists of three types of blocks (first to third blocks) in the shapes of rectangular parallelepipeds of the same width and thickness that are different in length along the axis direction which are arranged in a line orthogonal to the axis. For example, the first block 108*a* is about 60 mm long along the axis direction, the second block 108*b* is about 30 mm long, and the third block 108*c* is about 20 mm long.

Two axisymmetrical separate calibration blocks 106 for the right and left hands may be prepared, or a single calibration block 106 may be prepared to use for both the right and left hands by turning it over.

As shown in FIG. 20, a single block having a stepped portion 110 with multiple steps formed on one side thereof and a plane 112 formed on the other side may be provided, and in a state where the thumbs of the right and left hands touch the plane 112 of the block with being spaced a predetermined distance apart and where the index fingers of the right and left hands touch the stepped portion 110 of the block with being spaced a predetermined distance apart, calibration data may be obtained.

Where the pair of separate calibration blocks 106 or the single block having the stepped portion 110 is provided, there is the advantage that calibration data for the right and left hands of a subject can be obtained simultaneously. Where calibration data for both the hands of a subject is obtained simultaneously, by spacing the fingers of the right hand and those of the left hand a predetermined distance apart, interference between the motion sensors 22 for the right and left hands can be prevented.

Without using the calibration block 106 (106*a*), calibration data for a subject can be obtained with use of another device such as a calibration data detector using a variable resistance element.

Figure 22A:
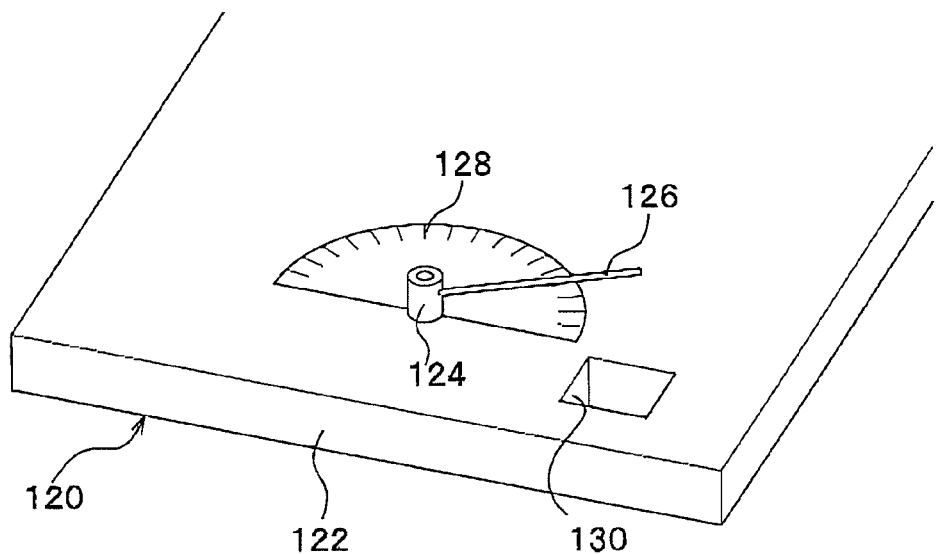
FIG. 22A is a perspective view of a calibration data detector.
Figure 22B:
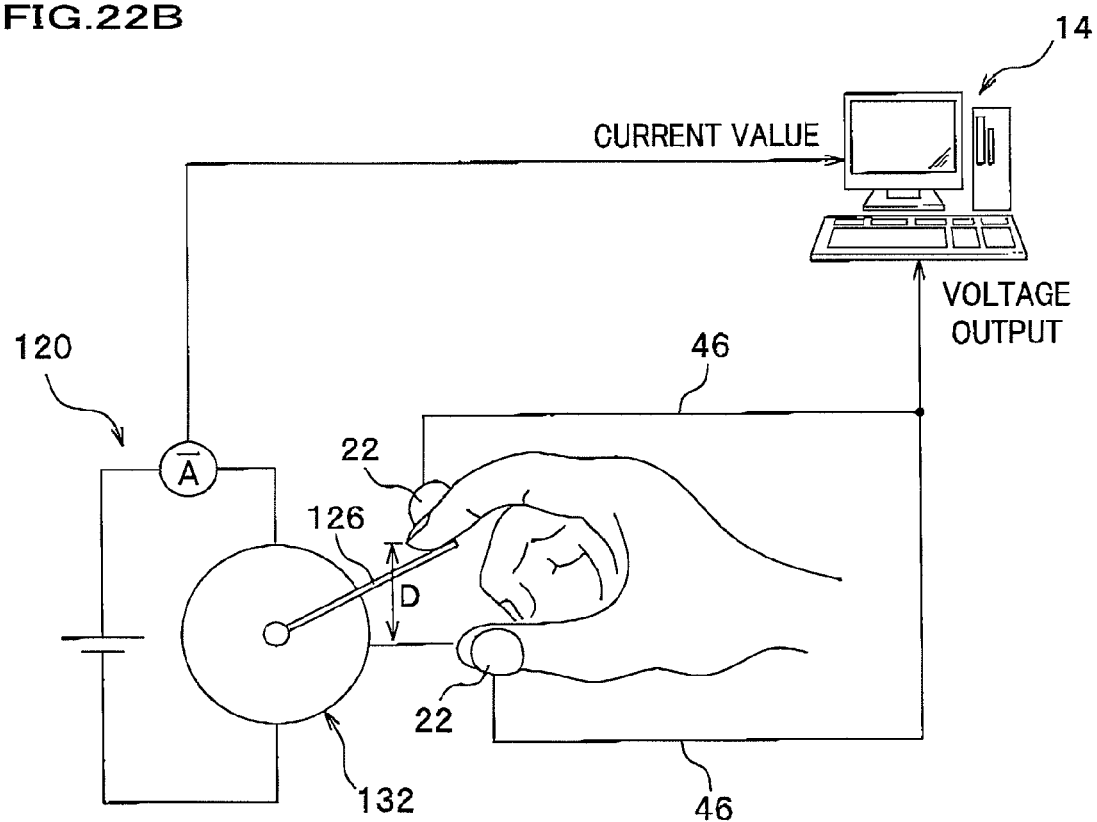
FIG. 22B is a circuit diagram of the calibration data detector.

FIG. 22A is a perspective view of a calibration data detector 120; FIG. 22B is a circuit diagram of the calibration data detector 120; and FIG. 23 is a plan, partially sectional view of a receiving coil substrate provided with an LC resonant circuit.

As shown in FIG. 22A, the calibration data detector 120 comprises a device body 122 comprises a rectangular block, a pivotable arm 126 provided on top of the device body 122 that is pivotable in an arc with a pin 124 as the pivot through a predetermined angle, a scale 128 provided on top of the device body 122 with which the angle of the pivotable arm 126 is seen, and a finger inserted hole 130 into which the thumb of the right or left hand of a subject is inserted and fixed. In the device body 122, there is provided a variable resistance element 132 coupled to the pivotable arm 126 that varies in resistance with the angle of the pivotable arm 126 (see FIG. 22B). As shown in FIG. 22B, a constant voltage is applied to the circuit of the calibration data detector 120, and by the subject pulling the pivotable arm 126 with the index finger while the thumb is inserted in the finger inserted hole 130, the motor function analyzing apparatus 14 obtains a current value (or a voltage value) at this time, thus obtaining angle information (distance D between the thumb and the index finger) of the pivotable arm 126 corresponding to the current value (or the voltage value). Furthermore, the motor function analyzing apparatus 14 obtains voltage outputs (voltage values) from the pair of motion sensors 22 attached to the thumb and the index finger, thus obtaining a correspondence between the voltage values from the motion sensors 22 and the distance D of the fingers of the subject. By obtaining the correspondences for a plurality of angles of the pivotable arm 126 while the subject pulls the pivotable arm 126 of the calibration data detector 120, calibration can be easily performed without using the calibration block 106 (106*a*).

Figure 23:
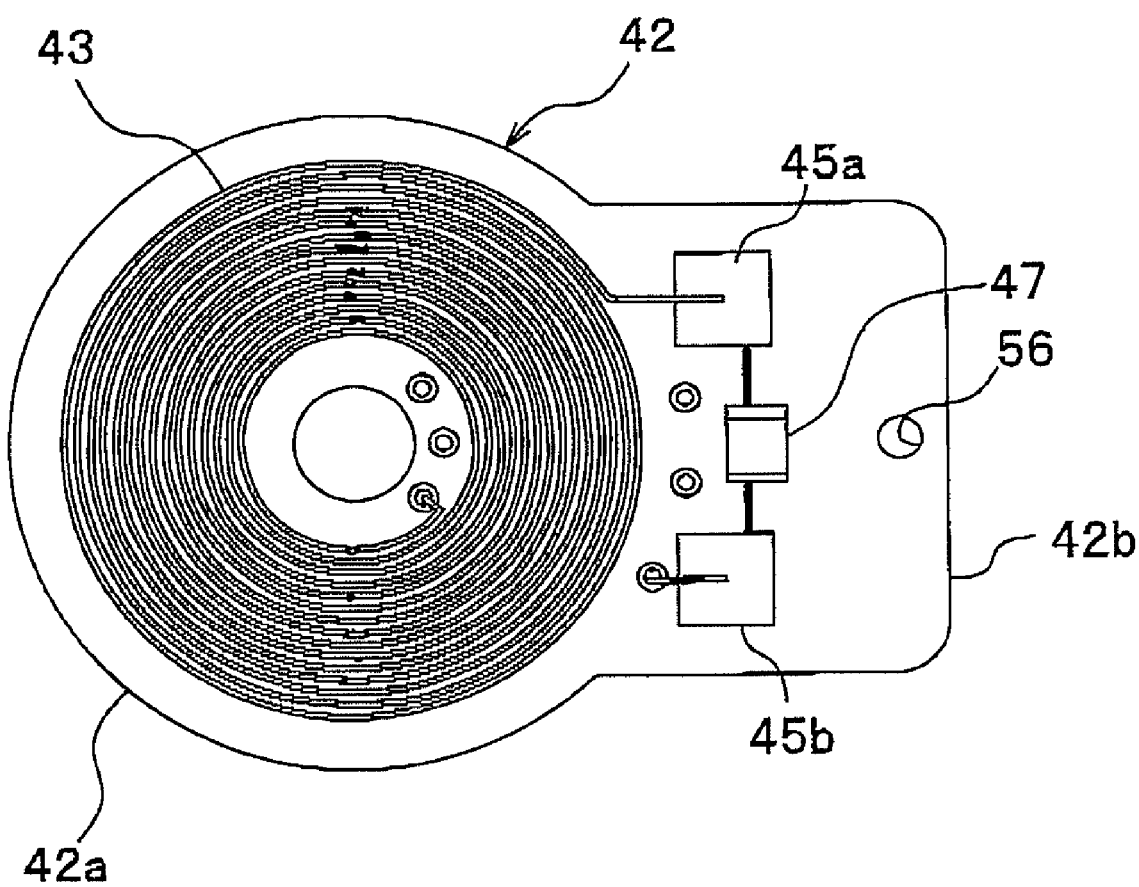
FIG. 23 is a plan, partially sectional view of a coil substrate provided with an LC resonant circuit.

As shown in FIG. 23, the coil substrate 42I, 42II, which function as a magnetic field generating unit or a magnetic field detecting unit, is a substrate such as a glass epoxy substrate or an FPC (Flexible Printed Circuit) substrate having six layers of coils 43 piled one on top of another (in FIG. 23, only the first layer of a coil 43 of the six layers is shown). One end of the coil 43 is electrically connected to a first pad 45*a* for connecting to the circuit, and the other end of the coil 43 is electrically connected to a second pad 45*b*, so that the coil 43 and the first and second pads 45*a*, 45*b* are serially connected. A chip capacitor 47 is connected between the first and second pads 45*a*, 45*b*, and an LC resonant circuit is formed where the capacitance (C) of the chip capacitor 47 and the inductance (L) of the coil 43 are connected in parallel. By setting the resonance frequency (f) of the LC resonant circuit to be the same as the frequency of the alternating current that is made to flow through the coil 43, sensitivity is improved to be about tenfold as compared with the case where the LC resonant circuit is not provided. In this condition, the resonance frequency (f) is expressed as $f=1/\sqrt{(2\pi LC)}$, and from this equation, the capacitance (C) is obtained as $C=1/(4\pi^2 f^2 L)$. Thus, the chip capacitor 47 of capacitance (C) satisfying this equation may be used. To be specific, when the inductance (L) of the coil 43 is about 60.8 μH and the resonance frequency (f) is 20 kHz, the capacitance (C) of the chip capacitor 47 is 1.04 μF. By providing the resonant circuit for the coil substrate 42 in this way, firstly, the sensitivity of the receiving coil is improved so as to be able to accurately measure even if the distance between the transmitting coil and the receiving coil is large, and secondly, the diameter of the coil 43 becomes smaller, so that the coil substrate 42 becomes smaller and lighter. As the inductance (L) of the coil 43 becomes smaller, by increasing the capacitance (C) of the chip capacitor 47, the coil substrate 42 becomes smaller and lighter. The coil substrate 42 provided with the resonant circuit is preferably used as the receiving coil 42II, but can be used as the transmitting coil substrate 42I as needed.

Figure 24A:
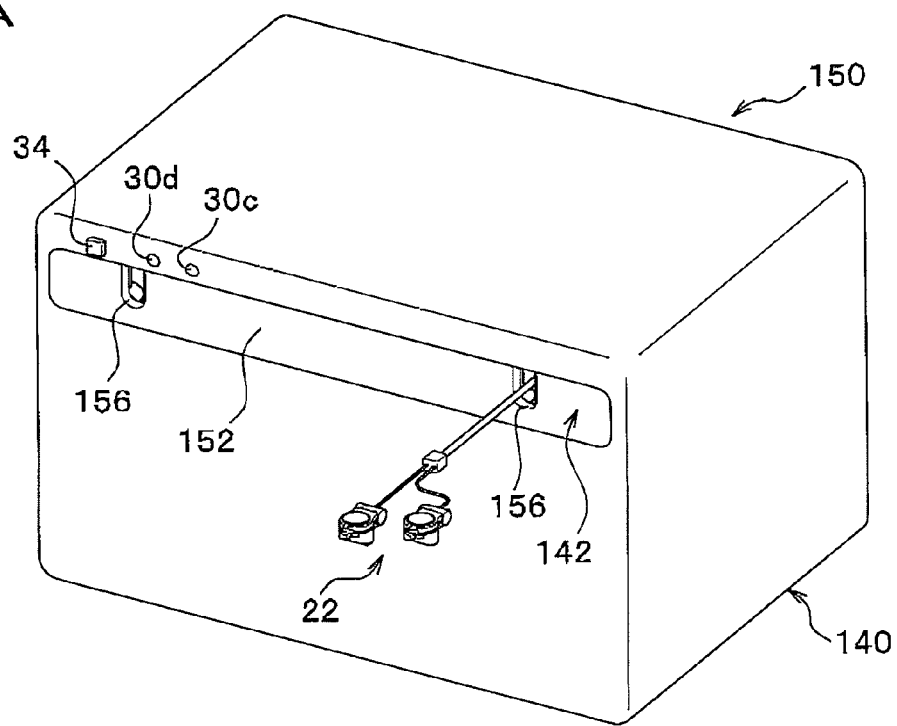
FIG. 24A is a perspective view of a motor function measuring apparatus according to another embodiment.
Figure 24B:
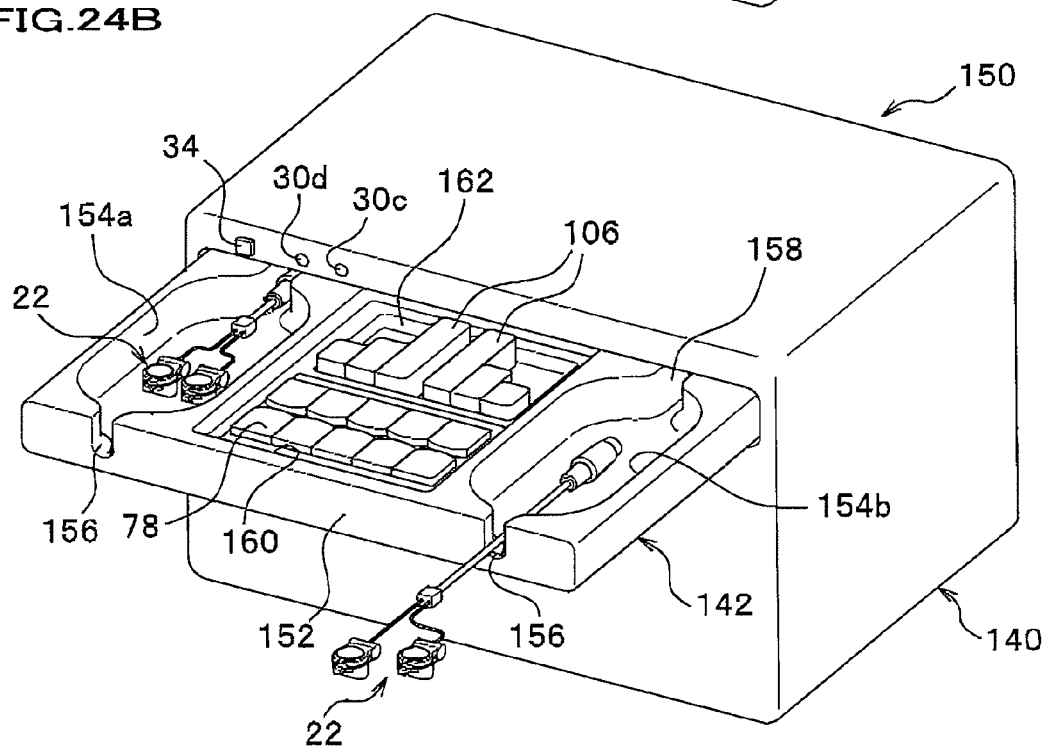
FIG. 24B is a perspective view showing the state where an containing unit has been drawn out of the body.

FIG. 24A is a perspective view of a motor function measuring apparatus 150 comprising an containing unit 142 assembled in a body 140 as another embodiment, and FIG. 24B is a perspective view showing the state where the containing unit 142 has been drawn out of the body 140.

The motor function measuring apparatus 150 according to the other embodiment differs from the motor function measuring apparatus 12 of FIG. 1 in that the containing unit 142 is assembled in the body 140. The same reference numerals indicate the same components as in the motor function measuring apparatus 12 with detailed description thereof being omitted.

The motor function measuring apparatus 150 comprises the box-like body 140 having an opening of a rectangular cross section made therein into which the containing unit 142 is inserted, and a slide member 152 that is inserted into the opening of the body 140 and that can be drawn out and pushed in horizontally.

As shown in FIG. 24B, first and second motion sensor containing spaces 154*a*, 154*b* for containing the right hand and left hand motion sensors 22 are provided in one end and the other end along the lateral direction of the slide member 152. Through-holes 156 of a substantially U-shaped cross section are made in the front of slide member 152 and in communication with the first and second motion sensor containing spaces 154*a*, 154*b* respectively. Therefore, the lead line 46 of the motion sensor 22 is made to extend through the through-hole 156 of the substantially U-shaped cross section, and thereby the slide member 152 can be inserted into the opening of the body 140 while the holder 40 is left outside the containing unit 142.

In other words, while the holder 40 remains pulled out, the slide member 152 can be contained in the opening of the body 140. Therefore, there is provided the motor function measuring apparatus 150 convenient in use by an operator.

A recess 158 is made in the side of the slide member 152 opposite to the through-holes 156 of the U-shaped cross section, and a connection terminal (not shown) electrically connected to the motion sensor controller 26 provided on the substrate in the body 140 is provided in the recess 158. Thus, the connector unit 48 of the lead line 46 forming part of the motion sensor 22 is attachable to and detachable from the connection terminal, and hence the motion sensor 22 can be easily replaced with a new one when degraded in endurance, and also maintenance can be easily performed.

Between the first and second motion sensor containing spaces 154a, 154b, there are provided an adhesive member containing space 160 for containing a plurality of adhesive members 78 piled one on top of another and a calibration block containing space 162 for containing the calibration block 106.

The motion sensor interface 24 (see FIG. 2) includes an analog-to-digital converter and converts the waveform data of an analog signal detected by the motion sensor 22 into waveform data of a digital signal at a predetermined sampling frequency. The converted digital signal is input to the motion sensor controller 26 (see FIG. 2).

Figure 26:
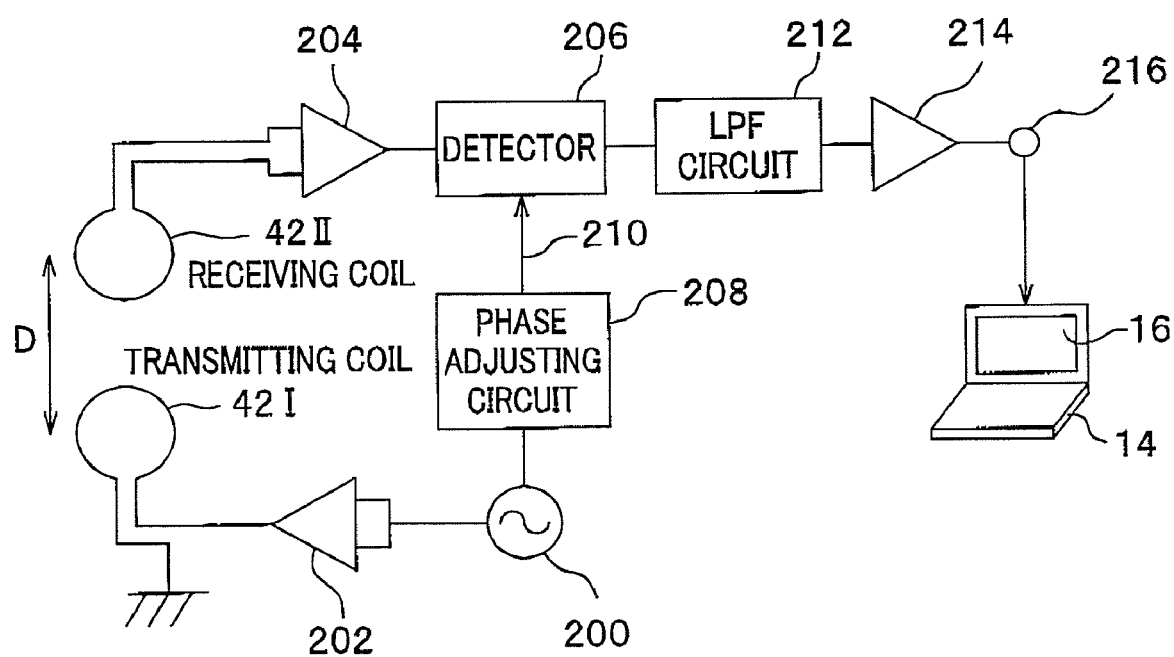
FIG. 26 is a block diagram showing the configuration of a motion sensor controller.

FIG. 26 is a block diagram of the motion sensor controller 26. A process of the motion sensor controller 26 obtaining waveform data will be described below.

In FIG. 26, an alternating current generating circuit (alternating current supplier) 200 generates an AC voltage of a specific frequency (e.g., 20 kHz). The AC voltage of the specific frequency is converted by a current generating amplifier 202 into an alternating current of the specific frequency, which is made to flow through the transmitting coil in the coil substrate 42I. The magnetic field generated by the transmitting coil induces an electromotive force in the receiving coil in the coil substrate 42II.

The induced electromotive force (of the same frequency as the AC voltage of the specific frequency generated by the alternating current generating circuit 200) is amplified by a preamplifier 204, and the amplified signal is input to a detector 206. The detector 206 detects at the specific frequency generated by the alternating current generating circuit 200 or at a frequency twice the specific frequency. Hence, a phase of the output of the alternating current generating circuit 200 is adjusted by a phase adjusting circuit 208 and then inputted as a reference signal 210 to a reference signal input terminal of the detector 206.

Where detecting at twice the specific frequency, the phase adjusting circuit 208 is not necessarily needed. A simple circuit configuration for detecting at twice the specific frequency is one where the specific frequency of the alternating current generating circuit 200 is set at the frequency twice the original specific frequency and divided into half the specific frequency, which is input to the current generating amplifier 202. A signal having a frequency twice the specific frequency of the alternating current generating circuit 200 may be input as the reference signal 210 to the reference signal input terminal of the detector 206.

The output signal of the detector 206 passes through an LPF (Low-Pass Filter) circuit 212 and is amplified by an amplifier 214 to obtain a desired voltage and input to the motor function analyzing apparatus 14. The output signal 216 of the amplifier 214 is a voltage corresponding to the distance D between the transmitting coil and the receiving coil attached to the thumb and the index finger respectively. The detector 206, the LPF circuit 212, and the amplifier 214 together function as a detected signal processing unit.

Although the case where the motion sensor 22 is of a magnetic sensor type has been described above, any sensor can be used as long as the sensor is one that measures the motion by use of the magnetic field generated. For example, a well known strain indicator or accelerometer may be used together with a magnetic sensor.

[Motor Function Analyzing Apparatus]

As shown in FIG. 2, the motor function analyzing apparatus 14 stores and analyzes data measured by the motor function measuring apparatus 12. The motor function analyzing apparatus 14 comprises a data input unit 320 to which the output signal of the motion sensor controller 26 is supplied and a data processing unit 300.

The data processing unit 300 analyzes the motor function of the subject based on the output signal supplied from the data input unit 320 and outputs the analyzed motor function together with information about the subject or the like to the display unit 16 as needed. The data processing unit 300 comprises a motion waveform generating part 302, a subject information processing part 304, and output processing part 306.

The data processing unit 300 comprises a computer (not shown) including a CPU (Central Processing Unit), a storage 310 including ROM (Read Only Memory), RAM (Random Access Memory), a hard disk, etc., and the like. Each part in the data processing unit 300 is provided by loading a program and data stored in the storage 310 into the computer (not shown), and each process of the data processing unit 300 is realized by the CPU reading a program from the storage 310 and executing it.

[Motion Waveform Generating Part]

The waveform data supplied from the motor function measuring apparatus 12 does not directly represent a motion waveform but is a voltage output corresponding to the motion waveform. The motion waveform generating part 302 converts this voltage output, i.e. waveform data, into a corresponding motion waveform, and time-differentiates or time-integrates the converted motion waveform, thereby generating a distance waveform, a speed waveform, an acceleration waveform, and a jerk waveform complementarily. The motion waveform includes at least one of the distance waveform, the speed waveform, the acceleration waveform, and the jerk waveform unless otherwise noted. Even where a strain indicator, an accelerometer, or the like is used for the motor function measuring apparatus 12, if at least one motion waveform is measured, other motion waveforms (distance, speed, acceleration, jerk) can be obtained complementarily by differentiating and integrating the motion waveform.

[Subject Information Processing Part]

The subject information processing part 304 (see FIG. 2) has a subject DB (Data Base) storing subject information, analysis results, and the like in the storage 310 and manages information stored in the subject DB.

To be more specific, the subject information processing part 304 performs the following four processes in cooperation with a subject: (1) registering, correcting, deleting, searching, and sorting subject information, (2) associating subject information with measurement data, (3) registering, correcting, and deleting results of analyzing the measurement data (adding, correcting, and deleting items), and (4), if statistic processing has been performed, registering, correcting, and deleting results of the statistic processing.

The subject information that is registered in the subject DB includes a subject ID, full name, birth date, age, height, weight, name of disease; comments about the subject, and the like. Information management by the subject information processing part 304 can be easily realized by a well known program and data.

[Output Processing Part]

The output processing part 306 displays information such as the subject information and the analysis results stored in the subject DB in easy-to-understand format visually on the display unit 16 using graphs or tables as needed. The output processing part 306 may not display all the analysis results simultaneously but display items selected by an operator.

[Display Unit]

The display unit 16 displays the subject information and motion information processed by the data processing unit 300 and embodied by, e.g., an LCD (Liquid Crystal Display), a CRT (Cathode Ray Tube), or a printer.

[Operation Input Unit]

The operation input unit 18 is used for an operator of the motor function measuring apparatus 12 to input subject information and embodied by a keyboard, a mouse, or the like. When inputting subject information, an entry screen image may be displayed as a user interface to assist the operator to input on the display.

[Example Screen images]

Next, example screen images displayed in the motor function measuring system 10 of the present embodiment will be described with reference to FIGS. 27 to 39. These screen images are displayed on the display unit 16 by the output processing part 306 in the data processing unit 300 of the motor function analyzing apparatus 14 instructing the display unit 16.

FIG. 27 is an example of a list screen image (measurement data list screen image 2700 (control screen image)) of measurement data in a main screen image. As shown in FIG. 27, the measurement data list screen image 2700 comprises a measurement data list portion 2702, a search condition inputting portion 2704, an operation (function) button portion 2706, and a screen image switch button portion 2708. In FIG. 27, "measurement data" in the screen image switch button portion 2708 has been selected and the measurement data list screen image 2700 is displayed. This screen image display application may be set to display the measurement data list screen image 2700 at the startup.

In the measurement data list portion 2702, "subject ID (Identification)", "full name", "measurement date", "measurement time", "measurement method", "age", "sex", "comment 1" and "comment 2" are displayed.

In the search condition inputting portion 2704, "subject ID", "full name", "sex", "age", "measurement date", "measurement method", "comment 1" and "comment 2" are displayed as search items and can be entered or selected. An operator of the motor function analyzing apparatus 14 (hereinafter simply called an "operator") can enter text into or select one, or ones, of these items so as to search. The search results are displayed in the measurement data list portion 2702.

The operation button portion 2706 includes as operations the following buttons (operators): "new measurement" button 2720 (a first operator) (for entering new subject information and measuring finger tapping), "measurement" button 2722 (a first operator) (for measuring finger tapping for an already selected subject), "data analysis" button 2724 (a second operator) (for displaying analysis information for data selected in the measurement data list portion 2702), "inter-annual display" button 2726 (a third operator) (for displaying an inter-annual graph for data selected in the measurement data list portion 2702), "measurement data deletion" (for deleting data selected in the measurement data list portion 2702), and "export" (for outputting analysis results for data selected in the measurement data list portion 2702 in CSV (Comma Separated Values) format). When any of them is selected, corresponding functions start. The "data analysis" button 2724, "inter-annual display" button 2726, "measurement data deletion", and "export" are performed to process data selected in the measurement data list portion 2702, and if no selected data exists or the selected data has been deleted, an error message may be displayed. Furthermore, if more than 100 search results exist, a display confirmation message may be displayed.

The operation button portion 2706 includes buttons as tools: "data management" (for editing data selected in the measurement data list portion 2702) and "option" (for setting default values for each screen image), and a button "end" (for ending the present application) in the bottom.

FIG. 28 is an example of a list screen image of subject data (subject data list screen image) in a main screen image. As shown in FIG. 28, the subject data list screen image comprises a subject data list portion 2802, a search condition inputting portion 2804, an operation (function) button portion 2806, and a screen image switch button portion 2708. In FIG. 28, "subject data" in the screen image switch button portion 2708 has been selected and the subject data list screen image is displayed.

In the subject data list portion 2802, "subject ID", "full name", "birth date", "sex", "dominant hand", and "memo" are displayed.

In the search condition inputting portion 2804, "subject ID", "full name", and "sex" are displayed as search items, and can be entered or selected. An operator can enter text into or select one, or ones, of these items so as to search. Then, by operating the "search start" button, the search starts, and by operating the "clear conditions" button, all set search conditions are cleared all together.

The operation button portion 2806 includes buttons for operating: "new measurement" button 2720 (a first operator) and "measurement" button 2722 (a first operator), which are the same as in the measurement data list screen image (see FIG. 27) and hence description thereof is omitted, and buttons as subject information settings: "addition" (for displaying a subject information setting screen image (see FIG. 29) to allow the operator to newly add a subject), "change" (for displaying the subject information setting screen image (see FIG. 29) concerning the subject selected in the subject data list portion 2802), and "deletion" (for deleting data selected in the subject data list portion 2802).

Further, the operation button portion 2806 includes buttons as tools: "data management" (for editing data selected in the subject data list portion 2802) and "option" (for setting default values for each screen image), and a button "end" (for ending the present application) in the bottom. When the buttons are selected, corresponding functions start.

FIG. 29 is an example of the subject information setting screen image, which is started by operating the "new measurement button" 2720 (see FIG. 27) in the main screen image.

As shown in FIG. 29, in the subject information setting screen image, "subject ID", "full name", "birth date", "sex", "dominant hand", and "memo" are displayed, and can be entered or selected. Some items such as "subject ID" and "full name" are preferably set to be indispensable items (an error message being displayed when not entered).

In the lower part, there are included buttons: "acquisition of information from subject ID" (for obtaining corresponding subject information registered in the subject DB based on the ID entered in the "subject ID" column, "save" (for saving the set contents and displaying a measurement setting screen image (see FIG. 30)), and "close" (for ending the subject information setting screen image and returning to the main screen image (see FIGS. 27, 28)).

FIG. 30 is an example of the measurement setting screen image. This measurement setting screen image 3000 (a measurement condition setting screen image) is started by operating the "measurement" button 2722 (see FIG. 27) in the main screen image.

As shown in FIG. 30, in the measurement setting screen image 3000, there are included: subject information 3002, measurement method 3004, measurement time interval 3006 (for setting a measurement time, where when "free" is selected, a text box comes to accept an entry and a value of 1 to 999 can be specified), calibration information 3008 (displaying calibration states of 20 mm, 30 mm, 60 mm, and maximum, where the background color is gray when not yet performed or white when already performed), and measurement comment 3010, and "setting of subject information" button 3012, a "setting for calibration" button 3014, "performing of measurement" button 3016, "analysis result" button 3018, and "end" button 3020 (for ending the measurement setting screen image 3000 and returning to the main screen image (see FIGS. 27, 28)).

By operating the "setting of subject information" button 3012, the subject information setting screen image (see FIG. 29; the "save" button can be changed to an "update" button in the display) is displayed, and each information item of the subject information 3002 can be set (updated).

The case where the "setting for calibration" button 3014 is operated will be described with reference to FIGS. 31, 32.

Figure 31A:
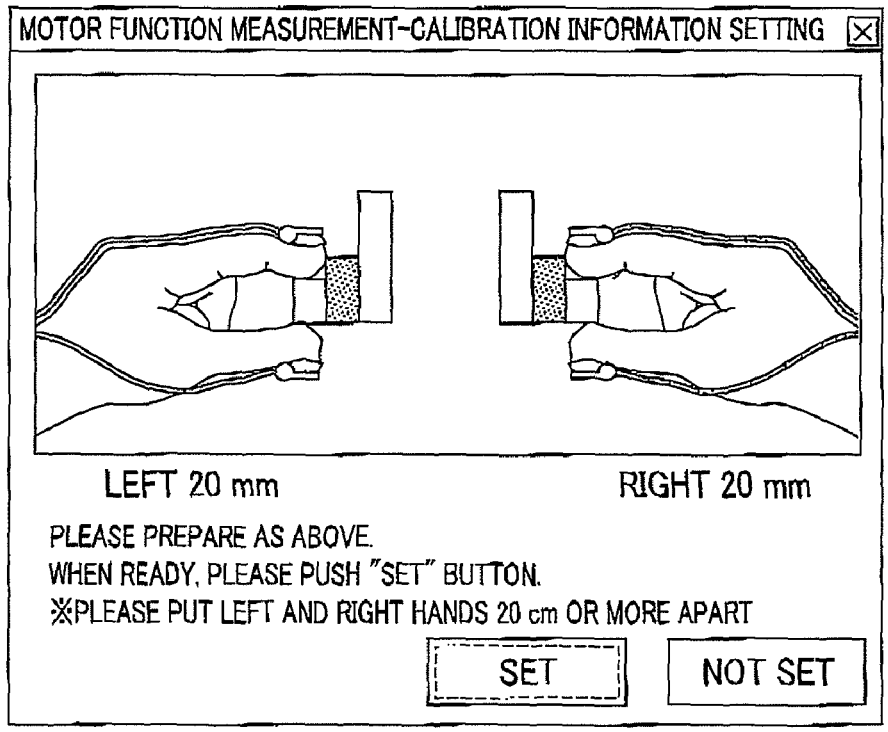
FIG. 31 shows an example of the screen image started when a setting-for-calibration button is operated.
Figure 31B:
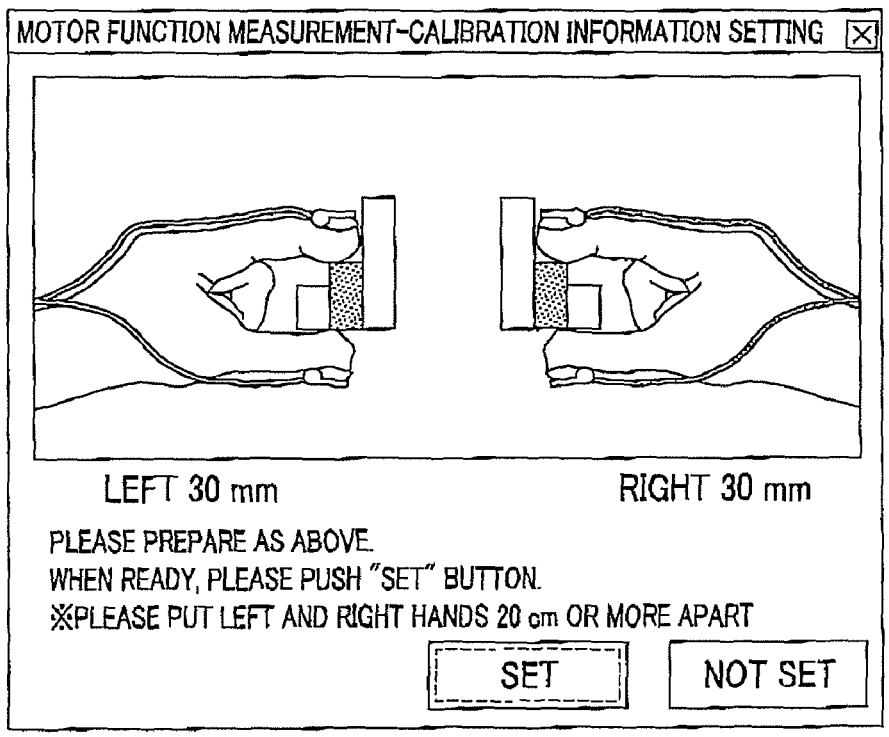
Figure 32A:
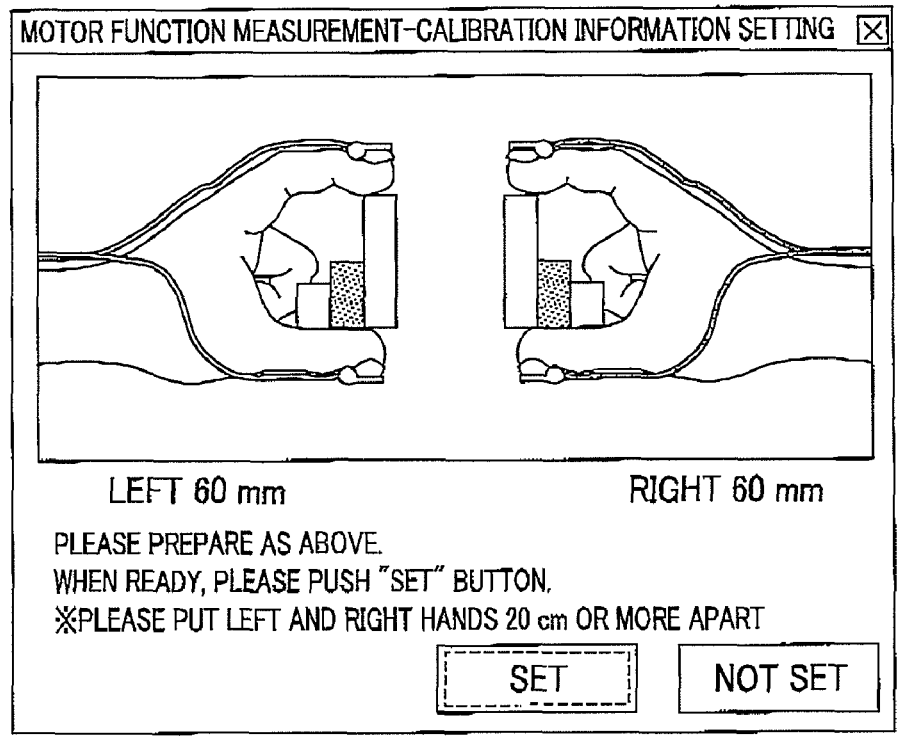
FIG. 32 shows an example of the screen image started when the setting-for-calibration button is operated.
Figure 32B:
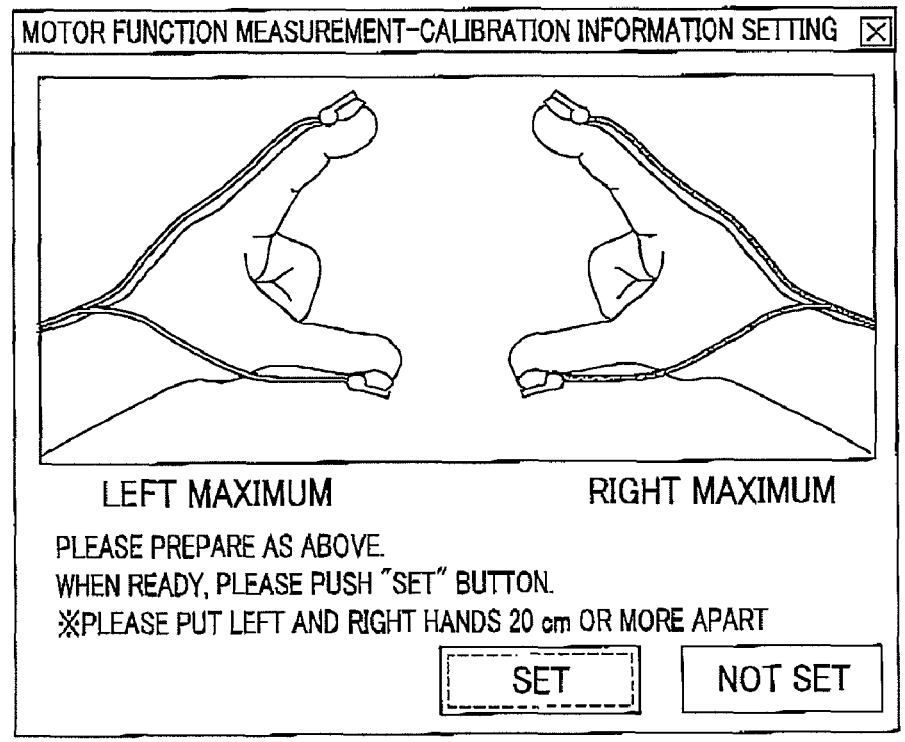

FIGS. 31, 32 show screen images started when the "setting for calibration" button 3014 (see FIG. 30) is operated, and the screen image shifts in the order of FIG. 31A to FIG. 31B to FIG. 32A to FIG. 32B. First, a screen image shown in FIG. 31A is displayed, and while a subject is holding the 20 mm parts of the calibration blocks 106 (see FIG. 19, etc.) with both hands, the operator operates on the "set" button, thereby allowing calibration to be performed, and the screen image shifts to a screen image shown in FIG. 31B. Likewise the shift occurs with FIG. 31B, FIG. 32A, and FIG. 32B, and hence description thereof is omitted.

FIG. 33 is an example of a performing-of-measurement screen image. This performing-of-measurement screen image is started by operating the "performing of measurement" button 3016 (see FIG. 30) in the measurement setting screen image.

As shown in FIG. 33, in the performing-of-measurement screen image, a right hand graph and a left hand graph (the horizontal axis representing seconds and the vertical axis representing the distance between the fingers) are displayed. By operating the "measurement start" button, measurement starts (starting the acquisition of data to be analyzed), and by operating the "measurement stop" button, measurement stops (stopping the acquisition of data to be analyzed). Besides, information about the subject to be measured (such as the subject ID) is displayed in the top right of the screen image.

The motor function analyzing apparatus 14 can convert voltage data obtained from the motor function measuring apparatus 12 into distance information based on calibration information and display it in the form of a graph.

In addition, in the performing-of-measurement screen image, there are included buttons: "metronome display" and "close" (close the present screen image), and a measurement time display bar (for displaying measurement time in the form of a progress bar). After measurement finishes, a confirmation message about saving the measured information may be displayed.

Figure 34:
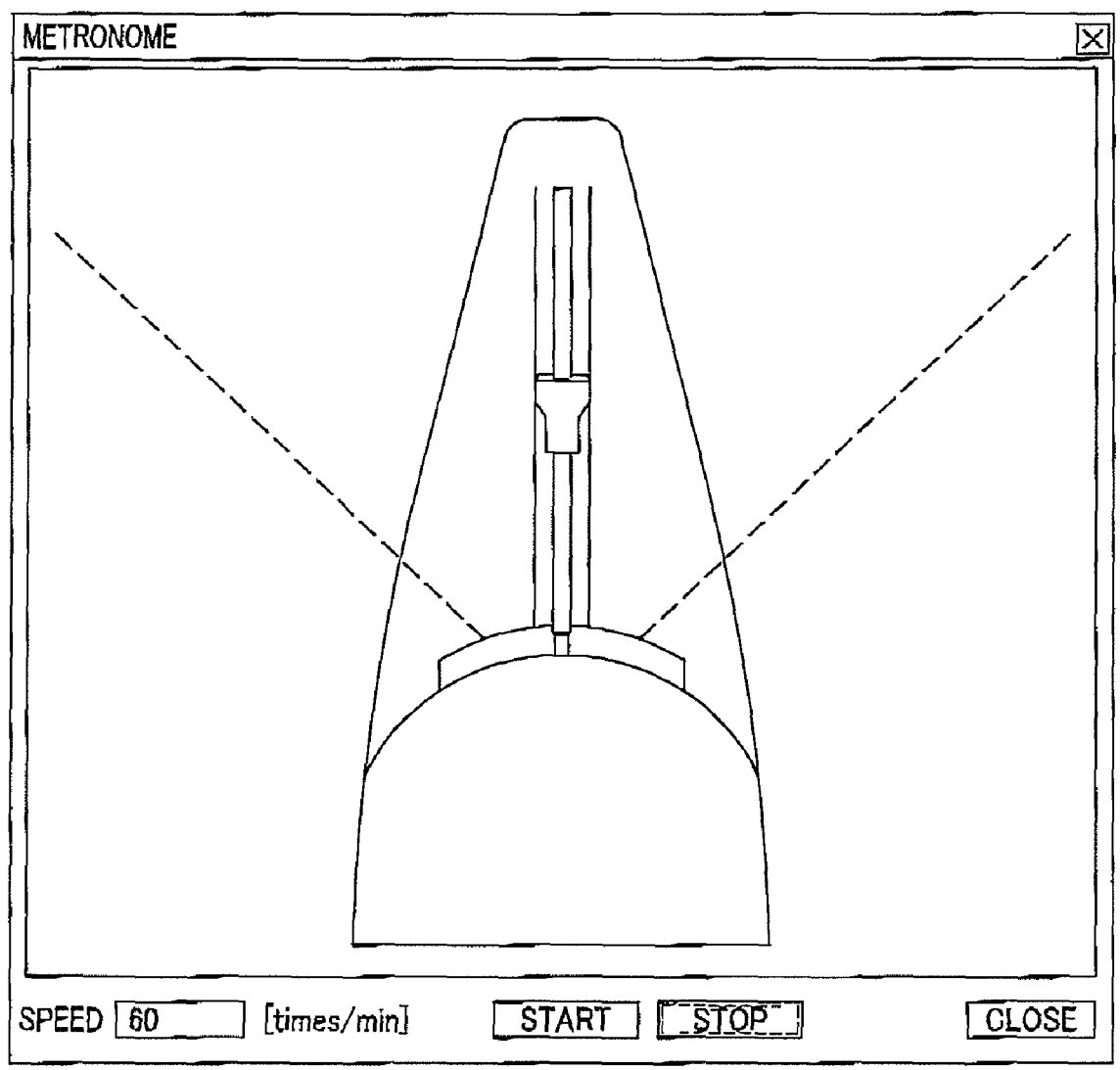
FIG. 34 shows an example of a metronome screen image.

FIG. 34 is an example of a metronome screen image as an auxiliary function for the performing of measurement. This metronome screen image is started by operating the "metronome display" (see FIG. 33) button in the performing-of-measurement screen image.

As shown in FIG. 34, in the metronome screen image, speed (times/minute) can be set, and by operating the "start" button, the metronome starts operating, and by operating the "stop" button, the metronome stops operating. By operating the "close" button, the present screen image is closed.

Figure 35:
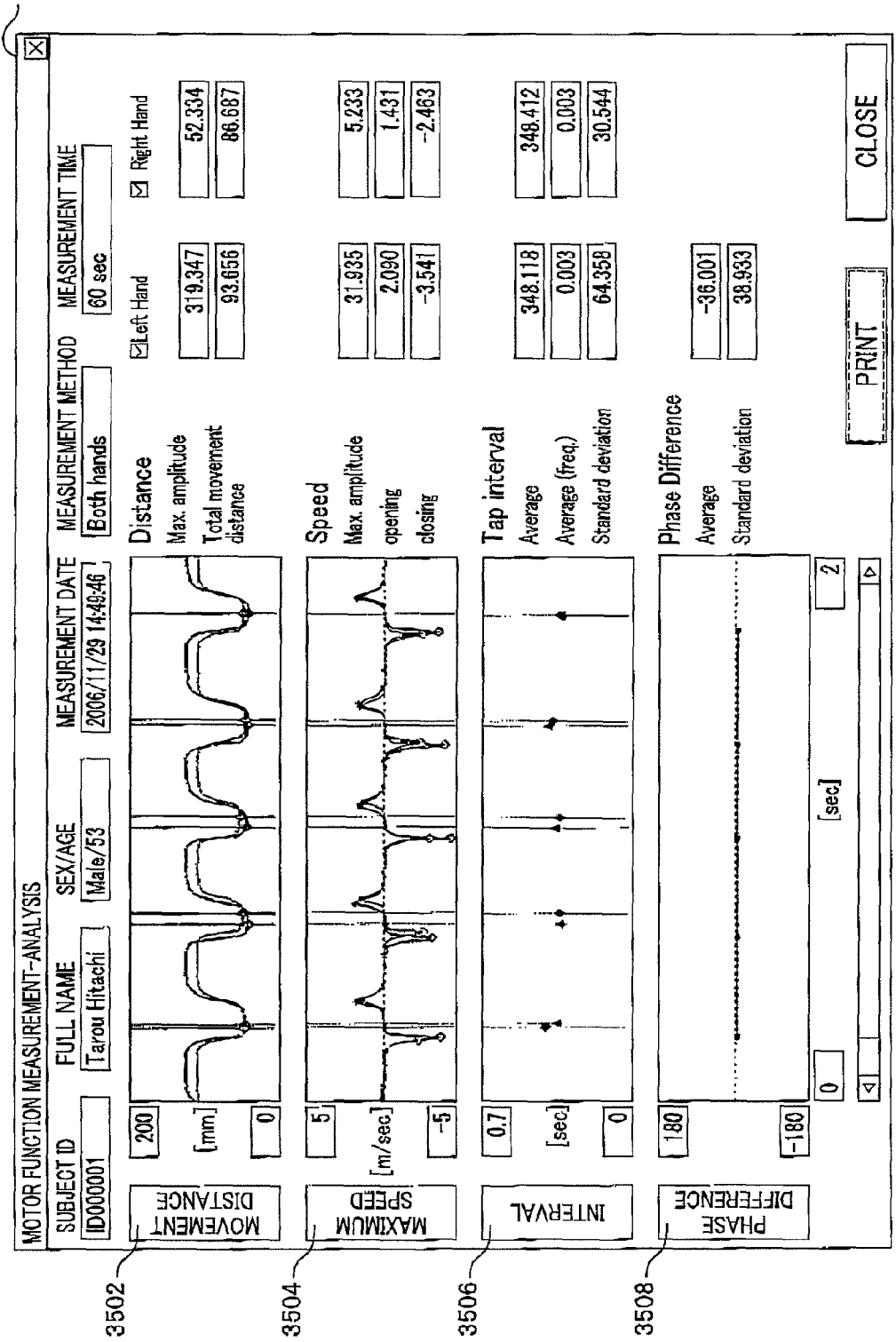
FIG. 35 shows an example of a measurement-data analysis result screen image.

FIG. 35 is an example of a measurement-data analysis result screen image 3500 (two seconds worth of data). By operating the "analysis result" button 3018 (see FIG. 30) in the measurement setting screen image, this analysis result screen image 3500 is automatically started after saving measurement data. In association with operating the "close" button (see FIG. 33) in the performing-of-measurement screen image, the analysis result screen image 3500 may be started to display analysis results for most recent measurement data. Besides, in the measurement data list screen image 2700 of FIG. 27, by operating the "data analysis" button 2724, the analysis result screen image 3500 of FIG. 35 may be displayed.

As shown in FIG. 35, in the analysis result screen image 3500, a movement distance 3502, maximum speed 3504, an interval 3506, and phase difference 3508 are each displayed in the form of a graph as data for a combination of "subject ID", "full name", "sex/age", "measurement date", "measurement method", and "measurement time" displayed in the top. The graphs can be switched in display between "only the left hand", "only the right hand", and "both hands" modes. Also, the analyzed values for each data are displayed on the right side of the screen image.

The movement distance 3502 is displayed in the form of a graph of distances calculated from saved measurement data, and the horizontal axis represents time (sec) and the vertical axis represents the distance (mm).

The maximum speed 3504 is displayed in the form of a graph of speeds calculated from the distances, and the horizontal axis represents time (sec) and the vertical axis represents the speed (m/sec). The "opening" refers to the average of maximum speeds when opening the hand, and the "closing" refers to the average of maximum speeds when closing the hand, which are each obtained through analysis.

The interval 3506 is displayed in the form of a graph of time lengths during which the distance stays at or around a minimum value, and the horizontal axis represents time (sec) and the vertical axis represents the time length of intervals (sec).

The phase difference 3508 is displayed in the form of a graph of phase differences calculated from distance data, etc., of both hands, and the horizontal axis represents time (sec) and the vertical axis represents the phase difference. If data for both hands do not exist, nothing is displayed.

By operating the "close" button, the present screen image is closed.

Figure 36:
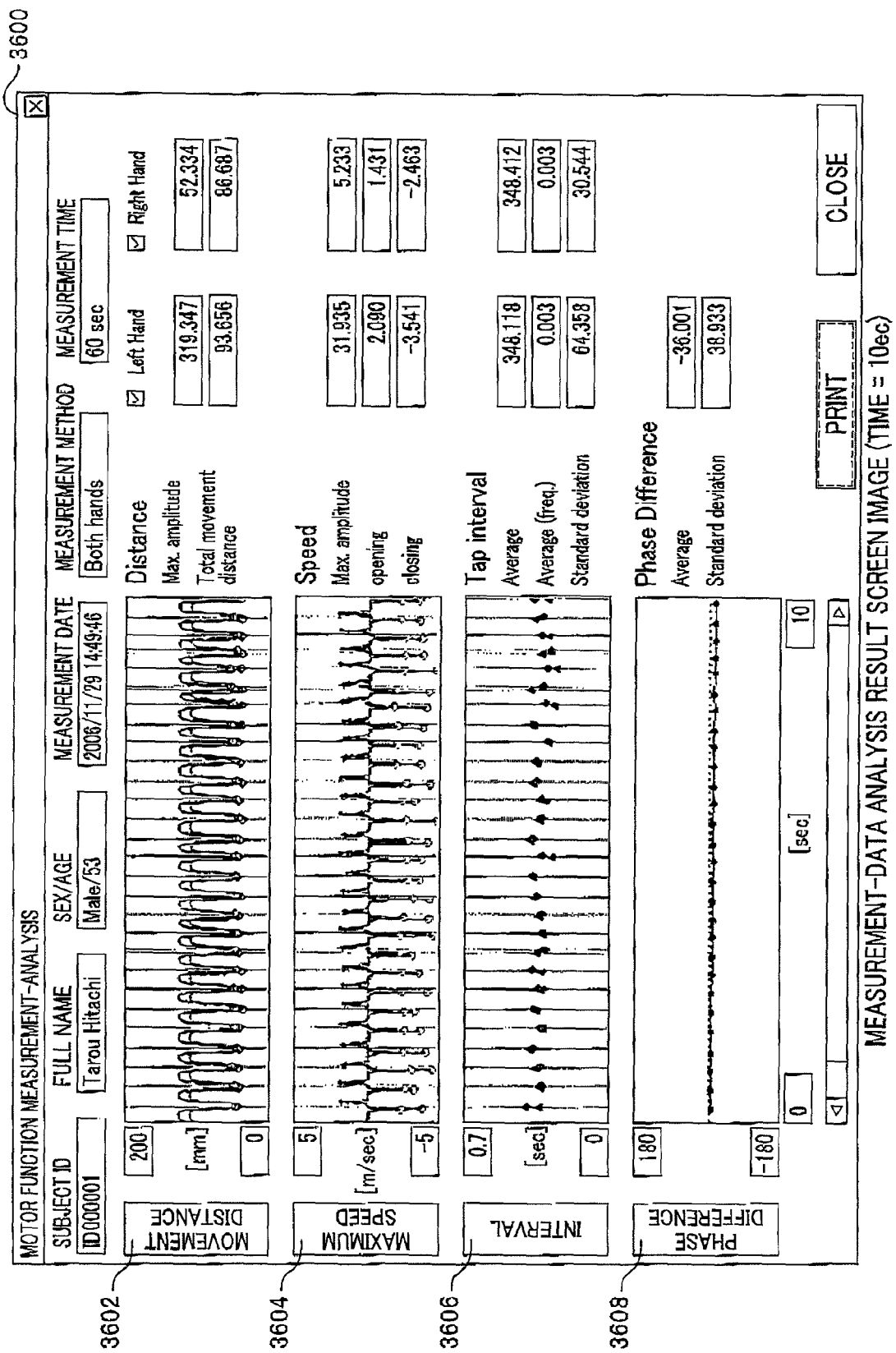
FIG. 36 shows an example of the measurement-data analysis result screen image.

FIG. 36 is an example of a measurement-data analysis result screen image 3500 (ten seconds worth of data). In this analysis result screen image, the movement distance 3602, maximum speed 3604, the interval 3606, and the phase difference 3608 are each displayed in the form of a graph. This analysis result screen image is the same as the screen image of FIG. 35 except that ten seconds worth of data is displayed, and hence description thereof is omitted.

Figure 37:
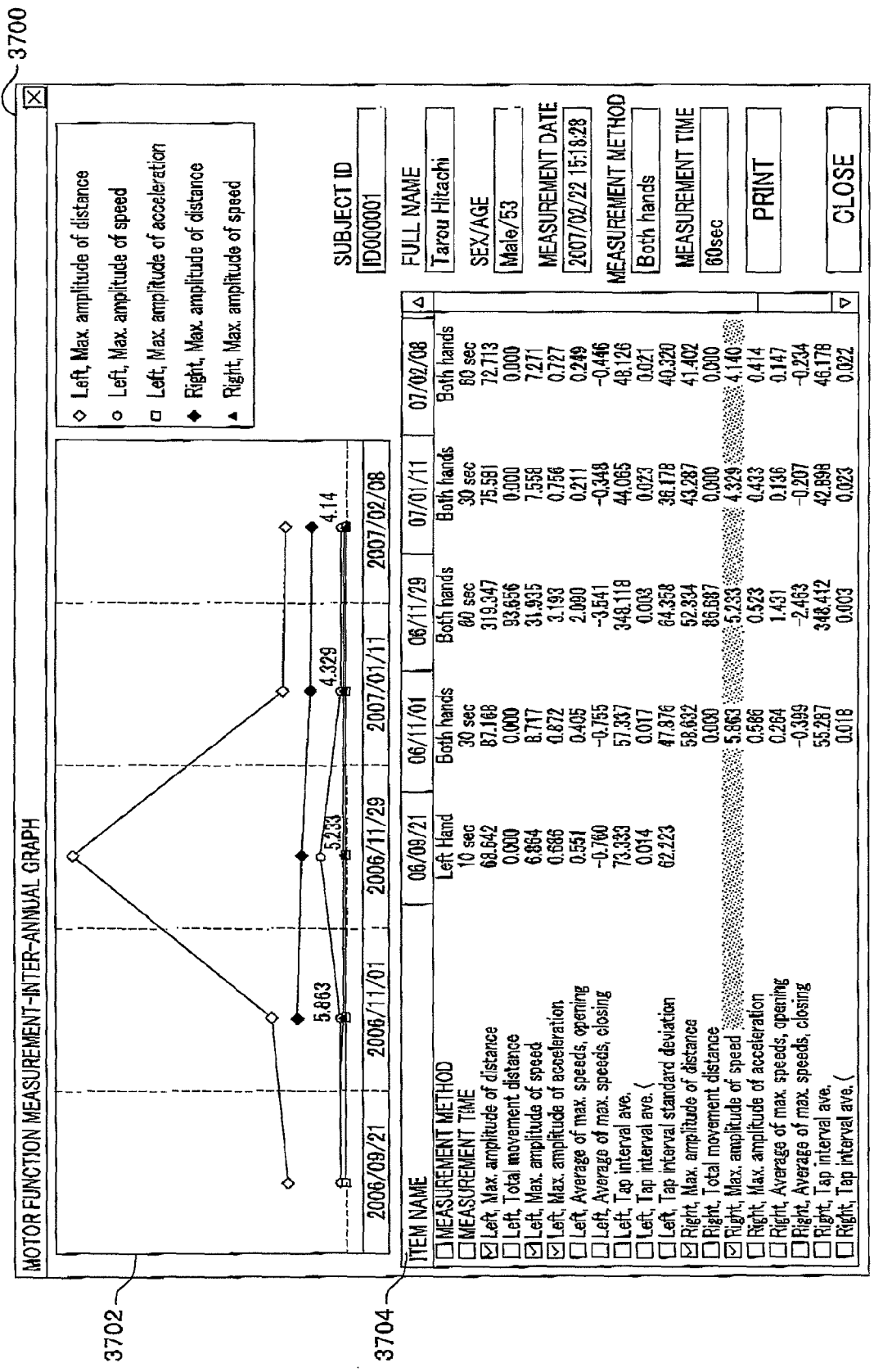
FIG. 37 shows an example of an inter-annual display screen image.

FIG. 37 is an example of an inter-annual display screen image. This inter-annual display screen image 3700 (a graph display screen image) is started by operating the "inter-annual display" button 2726 (see FIG. 27) in the measurement data list screen image.

As shown in FIG. 37, in the inter-annual display screen image 3700, there are included a graph portion 3702 and an item selecting portion 3704. In this screen image, data for a maximum of five items selected in the item selecting portion 3704 from among measurement data for a total of five measurement times or dates are displayed in the graph portion 3702 as data for a combination of "subject ID", "full name", "sex/age", "measurement date", "measurement method", and "measurement time" displayed in the right side.

By operating the "print" button, information of the graph portion 3702 is printed by a printer (not shown) or the like. By operating the "close" button, the present screen image is closed.

Figure 38:
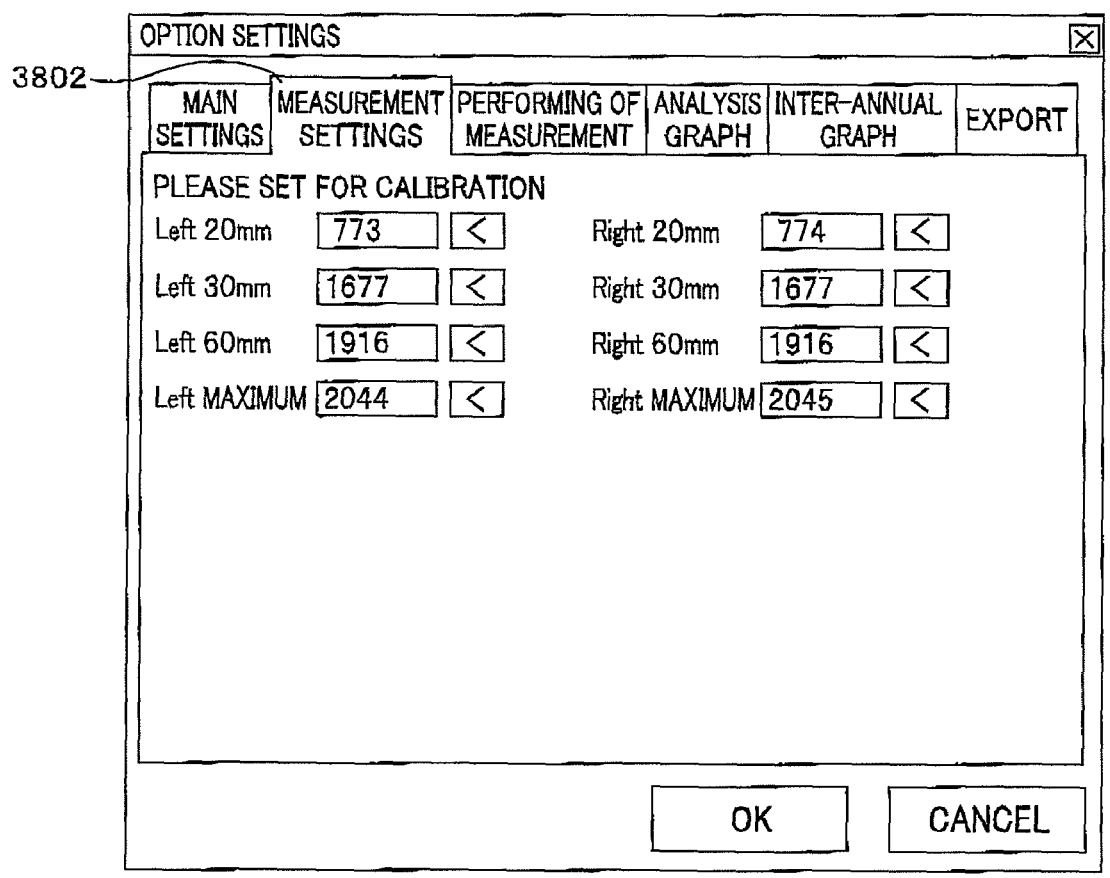
FIG. 38 shows an example of an option setting screen image.

FIG. 38 is an example of an option setting screen image. This option setting screen image is started by operating the "option" button (see FIG. 27) in the measurement data list screen image 2700.

As shown in FIG. 38, if the tab of measurement setting 3802 is selected in the option setting screen image, initial values for calibration can be set. Each item accepts only numerical values, and if NULL, an error is notified.

Figure 39:
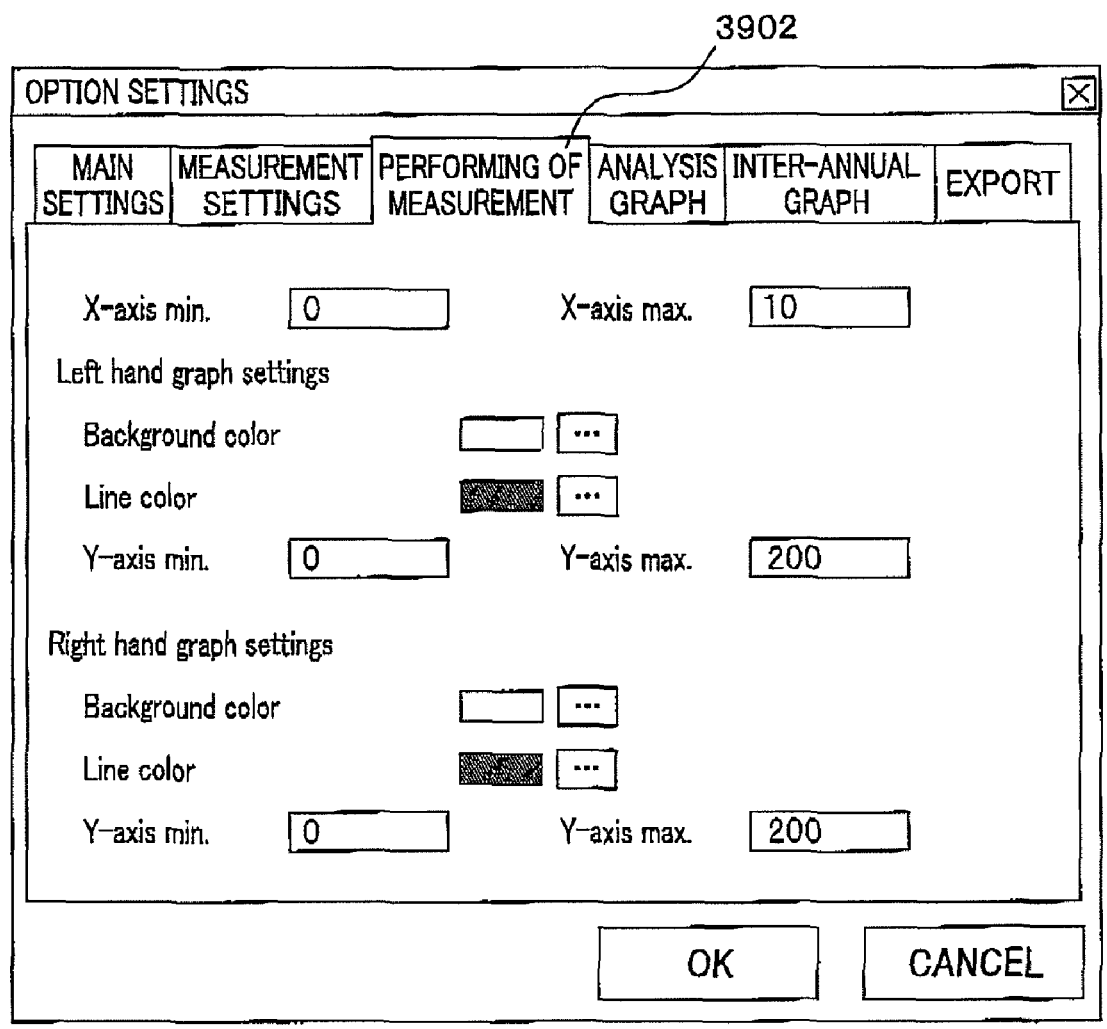
FIG. 39 shows another example of the option setting screen image.

FIG. 39 is another example of the option setting screen image. As shown in FIG. 39, if the tab of performing of measurement 3902 is selected in the option setting screen image, the value of each item in the performing-of-measurement screen image (see FIG. 33) can be set. The background color is, e.g., white for both right and left hands when no setting. Further, the line color is, e.g., blue for the left hand and red for the right hand when no setting. The X-axis minimum, X-axis maximum, Y-axis minimum, and Y-axis maximum accept only numerical values.

By using the screen images shown in FIGS. 27 to 39 and the like in the above way, the motor function measuring system 10 of the present embodiment can be realized.

What is claimed is:

1. A motor function measuring sensor including a right hand sensor and a left hand sensor so as to measure motor function of fingers of a subject, each of the right hand sensor and the left hand sensor, comprising:
   a magnetic field generating unit for generating a magnetic field;
   a magnetic field detecting unit for detecting the magnetic field;
   a first holder to be attached to a first predetermined part of a living body for holding the magnetic field generating unit;
   a second holder to be attached to a second predetermined part of the living body for holding the magnetic field detecting unit, a distance between the first and second parts being variable by motion of the living body; and
   a sticking part, the magnetic field detecting unit outputting a measurement signal based on an intensity of the detected said magnetic field to detect a motor function of the living body,
   a distinguishing part for distinguishing the sensor to be used between the right hand and left hand of the living body, and
   an electric wire electrically connected to the magnetic field generating unit and the magnetic field detecting unit, wherein the electric wire has a connector unit including a plurality of pins as the distinguishing part and at least one of the first holder and the second holder includes an attachment surface, the sticking part detachably attaches the attachment surface to the living body,
   wherein there is a difference in a number of the pins between the right hand sensor and the left hand sensor.

2. The motor function measuring sensor according to claim 1, wherein the sticking part comprises a seat including adhesive surfaces on its front and back sides, respectively.

3. The motor function measuring sensor according to claim 2, wherein the seat comprise a tab having non-adhesive surfaces.

4. The motor function measuring sensor according to claim 1, wherein the attachment surface comprises a slit along an axis direction across the attachment surface.

5. The motor function measuring sensor according to claim 1, wherein each of the first and second holders comprises:
   an upper holder and a lower holder;
   a coil substrate including a through hole into which the electric wire is inserted and the electric wire is electrically connected to a circuit on the substrate.

6. The motor function measuring sensor according to claim 1, further comprises:
   a character or a mark indicating either of the right hand or the left hand of the living body.

7. The motor function measuring sensor according to claim 1, further comprises:
   the distinguishing part including a color on an outer surface of the electric wire for indicating either of the right hand or the left hand of the living body.

8. The motor function measuring sensor according to claim 1,
   wherein the number of the pins is either a first value for the right hand or a second value for the left hand, which is different from the first value.

9. The motor function measuring sensor according to claim 1, further comprises:
   a string member including an engaging part for engaging with the electric wire, the engaging part being slidable relative the electric wire; and
   a clip for clipping a part of clothes of the living body.

* * * * *